US009012508B2

(12) United States Patent
Pavliv

(10) Patent No.: US 9,012,508 B2
(45) Date of Patent: Apr. 21, 2015

(54) ADMINISTRATION OF INTRAVENOUS IBUPROFEN

(75) Inventor: Leo Pavliv, Cary, NC (US)

(73) Assignee: Cumberland Pharmaceuticals, Nashville, TN (US)

( * ) Notice: Subject to any disclaimer, the term of this patent is extended or adjusted under 35 U.S.C. 154(b) by 186 days.

(21) Appl. No.: 12/722,682

(22) Filed: Mar. 12, 2010

(65) Prior Publication Data
US 2010/0234465 A1 Sep. 16, 2010

Related U.S. Application Data

(60) Provisional application No. 61/159,585, filed on Mar. 12, 2009.

(51) Int. Cl.
A01N 37/10 (2006.01)
A61K 31/19 (2006.01)
A01N 37/12 (2006.01)
A01N 37/44 (2006.01)
A61K 31/192 (2006.01)
A61K 31/485 (2006.01)

(52) U.S. Cl.
CPC ............ *A61K 31/192* (2013.01); *A61K 31/485* (2013.01)

(58) Field of Classification Search
USPC ........................................................ 514/570
See application file for complete search history.

(56) References Cited

U.S. PATENT DOCUMENTS

| | | | |
|---|---|---|---|
| 4,279,926 A | 7/1981 | Bruzzese | |
| 4,309,421 A | 1/1982 | Ghyczy | |
| 4,859,704 A | 8/1989 | Haas | |
| 4,861,797 A | 8/1989 | Haas | |
| 5,200,558 A | 4/1993 | Kkwan | |
| 5,463,117 A | 10/1995 | Stroppolo | |
| 6,005,005 A | 12/1999 | Stroppolo | |
| 6,342,530 B1 | 1/2002 | Darko | 514/561 |
| 6,423,746 B1 | 7/2002 | Yarbrough | 514/561 |
| 6,727,286 B2 | 4/2004 | Pavliv | 514/565 |
| 2003/0100612 A1 | 5/2003 | Pavliv | |
| 2004/0132823 A1 | 7/2004 | Pavliv | 514/565 |
| 2004/0253244 A1* | 12/2004 | Shelton et al. | 424/145.1 |
| 2006/0142181 A1 | 6/2006 | Miller | |
| 2008/0058302 A1 | 3/2008 | Dolle et al. | |
| 2009/0048345 A1 | 2/2009 | Lee | 514/570 |
| 2009/0054413 A1* | 2/2009 | Henriksson et al. | 514/221 |
| 2010/0015237 A1 | 1/2010 | Moses et al. | |
| 2010/0234465 A1 | 9/2010 | Pavliv | |
| 2011/0028553 A1 | 2/2011 | Pavliv | |
| 2011/0028556 A1 | 2/2011 | Pavliv | |
| 2011/0028557 A1 | 2/2011 | Pavliv | |
| 2011/0028558 A1 | 2/2011 | Pavliv | |

FOREIGN PATENT DOCUMENTS

| | | |
|---|---|---|
| CN | 1871028 A | 11/2006 |
| CN | 101217939 A | 7/2008 |
| DE | 19912436 | 9/2000 |
| JP | H11-512081 | 10/1999 |
| JP | 2006-525960 | 11/2006 |
| WO | WO97/04780 | 2/1997 |
| WO | WO 03039532 | 5/2003 |
| WO | WO2004/073653 | 9/2004 |
| WO | WO2006126214 A2 | 11/2006 |

OTHER PUBLICATIONS

Lamprecht et al. (Lipid nanocarriers as drug delivery system for ibuprofen in pain treatment. Int J Pharm. Jul. 8, 2004;278(2):407-14).*
Payne et al. (The relationship of preoperative and intraoperative factors on the incidence of pain following ambulatory surgery. Ambulatory Surgery. vol. 3, Issue 3, Sep. 1995,abstract).*
Thayer et al. (Effects of ibuprofen on postoperative bowel motility and propulsion. Diseases of the Colon & Rectum 31.5 (1988): 363-367).*
Owen et al. (Ibuprofen in the management of postoperative pain. Br J Anaesth. Dec. 1986;58(12):1371-5).*
Singla, N., et al. "A Multi-Center, Randomized, Double-Blind Placebo-Controlled Trial of Intravenous-Ibuprofen (IV-Ibuprofen) for Treatment of Pain in Post-Operative Orthopedic Adult Patients," Pain Med. Aug. 2010; 11(8): 1284-1293.
Singla, N,, et al., Poster, Ibid.
Dionne, R., et al, "Evaluation of preoperative ibuprofen for postoperative pain after removal of third molars." Oral Surg. Oral Med. Oral Pathol. Jun. 1978;45(6):851-6.
Dionne, R., et al, "Use of Ibuprofen in dentistry" Ibuprofen, A Critical Bibliographic Review, edited by K.D. Rainsford, Chapter 8,2.1., Taylor & Francis, 1999.
Campbell W., et al, "Intravenous diclofenac sodium: does its administration before operation suppress postoperative pain?" Anaesthesia. 1990; 45: 763-6.
Maunuksela et al, "Efficacy of rectal ibuprofen in controlling postoperative pain in children" Canadian Journal of Anaesthesia, Mar. 1992, vol. 39, Issue 3, pp. 226-230.
Ræder, Johan C., et al. "Oral ibuprofen versus paracetamol plus codeine for analgesia after ambulatory surgery." Anesthesia & Analgesia 92.6 (2001): 1470-1472.
International Search Report, mailed on Oct. 25, 2013, issued by the European Patent Office in corresponding EP Application No. 10751461,4.
Third Party Observations, mailed on Jul. 25, 2013, issued by the European Patent Office in corresponding EP Application No. 10751461.4.
International Search Report, mailed on Apr. 1, 2013, issued by the PCT in commonly-owned PCT Application No. PCT/US13/22519.

(Continued)

*Primary Examiner* — Layla Soroush
(74) *Attorney, Agent, or Firm* — Davidson, Davidson & Kappel LLC

(57) ABSTRACT

An effective dose of intravenous ibuprofen administered every 6 hours in surgery patients is a safe and effective way to reduce both pain and the need for morphine. In preferred embodiments, the administration of intravenous ibuprofen starts with the onset of anesthesia.

5 Claims, No Drawings

(56) References Cited

OTHER PUBLICATIONS

Ruth E. Bennie et al: "Postoperative analgesia with preoperative oral ibuprofen on acetaminophen in children undergoing myringotomy", Paediatric Anaestesia, Feb. 12, 1997, pp. 399-403, XP55031201, Retrieved from the Internet: URL:http://onlinelibrary.wiley.com/doi/10.1046/j.1460-9592.1997.d01-115.x/pdf [retrieved on Jun. 27, 2012].

Van Dyke T et al: "Combination oxycodone 5 mg/ibuprofen 400 mg for the treatment of postoperative pain: A double-blind, placebo- and active-controlled parallel-group study", Clinical Therapeutics, Excerpta Medica, Princeton, NJ, US, vol. 26, No. 12, Dec. 1, 2004, pp. 2003-2014, XP004780661, ISSN: 0149-2918, DOI: 10.1016/J.Clinthera.2004.12.002.

Charles Bankhead: "SCCM: IV Ibuprofen Controls Fever in Critically Ill Patients", Internet Citation, Feb. 3, 2009, p. 1, XP008151826, Retrieved from the Internet: URL:http://www.medpagetoday.com/MeetingCoverage/SCCM/12728 [retrieved on May 10, 2012].

Anonymous: "prescribing information of CALDOLOR", , Jun. 1, 2009, XP55030543, Retrieved from the Internet: URL:http://caldolor.com/pdfs/Prescribing_Information.pdf [retrieved on Jun. 20, 2012].

Supplementary European Search Report and Written Opinion, dated Jun. 29, 2012, issued in connection with corresponding International Patent Application No. PCT/US10/027096.

Office Action dated Apr. 16, 2012, issued in connection with corresponding U.S. Appl. No. 12/830,991.

Applicant's Response to Office Action dated Oct. 28, 2011, issued in connection with corresponding U.S. Appl. No. 12/830,991.

Applicant's Response to Office Action dated Nov. 10, 2010, issued in connection with corresponding U.S. Appl. No. 12/830,991.

Applicant's Response to Office Action dated Sep. 28, 2010, issued in connection with corresponding U.S. Appl. No. 12/830,991.

Applicant's Supplemental Amendment, dated Sep. 27, 2010, in connection with corresponding U.S. Appl. No. 12/830,991.

Applicant's Response to Office Action dated Aug. 9, 2010, issued in connection with corresponding U.S. Appl. No. 12/830,991.

Office Action dated Oct. 28, 2011, issued in connection with corresponding U.S. Appl. No. 12/830,991.

Applicant's Response to Office Action dated Sep. 8, 2011, issued in connection with corresponding U.S. Appl. No. 12/830,991.

Office Action dated Sep. 8, 2011, issued in connection with corresponding U.S. Appl. No. 12/830,991.

Office Action dated Jul. 13, 2011, issued in connection with corresponding U.S. Appl. No. 12/830,991.

Interview dated May 11, 2011, issued in connection with corresponding U.S. Appl. No. 12/830,991.

Office Action dated Mar. 9, 2011, issued in connection with corresponding U.S. Appl. No. 12/830,991.

Advisory Action dated Mar. 9, 2011, issued in connection with corresponding U.S. Appl. No. 12/830,991.

Interview dated Dec. 6, 2010, issued in connection with corresponding U.S. Appl. No. 12/830,991.

Office Action dated Nov. 10, 2010, issued in connection with corresponding U.S. Appl. No. 12/830,991.

Applicant's Terminal Disclaimer filed Oct. 27, 2010, in connection with corresponding U.S. Appl. No. 12/830,991.

Office Action dated Sep. 28, 2010, issued in connection with corresponding U.S. Appl. No. 12/830,991.

Applicant's Supplemental Amendment, dated Sep. 27, 2010, issued in connection with corresponding U.S. Appl. No. 12/830,991.

Office Action dated Aug. 9, 2010, issued in connection with corresponding U.S. Appl. No. 12/830,991.

Office Action dated Jul. 9, 2010, issued in connection with corresponding U.S. Appl. No. 12/830,991.

Applicant's Petition filed Jul. 6, 2010, in connection with corresponding U.S. Appl. No. 12/830,991.

Office Action dated May 23, 2012, issued in connection with the corresponding U.S. Appl. No. 12/646,499.

Applicant's Response to Office Action dated Aug. 25, 2011, issued in connection with the corresponding U.S. Appl. No. 12/646,499.

Office Action dated Aug. 25, 2011, issued in connection with the corresponding U.S. Appl. No. 12/646,499.

Applicant's Preliminary Amendment dated Sep. 27, 2010, issued in connection with the corresponding U.S. Appl. No. 12/646,499.

Applicant's Response to Office Action dated Jan. 13, 2010, issued in connection with the corresponding U.S. Appl. No. 12/646,499.

Office Action dated Jan. 13, 2010, issued in connection with the corresponding U.S. Appl. No. 12/646,499.

Office Action dated Jul. 27, 2012, issued in connection with the corresponding U.S. Appl. No. 12/699,595.

Applicant's Response to Office Action dated Sep. 20, 2011, filed in connection with corresponding U.S. Appl. No. 12/699,595.

Office Action dated Sep. 20, 2011, issued in connection with the corresponding U.S. Appl. No. 12/699,595.

Applicant's Preliminary Amendment dated Sep. 27, 2010, filed in connection with corresponding U.S. Appl. No. 12/699,595.

Applicant's Response to Notice of Missing Parts dated Feb. 24, 2010, issued in connection with the corresponding U.S. Appl. No. 12/699,595.

Notice of Missing Parts dated Feb. 24, 2010, issued in connection with the corresponding U.S. Appl. No. 12/699,595.

U.S. Appl. No. 13/422,738, Pavliv.

Bayouth et al. "713: Early Intravenous Ibuprofen Decreases Narcotic Requirement and Length of Stay Following Traumatic Rib Fractures". Crit. Care Med. Dec. 2011; 39(12 Suppl.):199.

Bayouth et al. [Online] Poster Presentation: "713: Early Intravenous Ibuprofen Decreases Narcotic Requirement and Length of Stay Following Traumatic Rib Fractures" [Retrieved Jun. 6, 2013]. Retrieved from the Internet: <URL: http://www.surgicalcriticalcare.net/Images/ibuprofen%20poster.pdf>. Presented at the Society of Critical Care Medicine: 41$^{st}$ Annual Congress, Feb. 4-8, 2012, Houston, Texas. One page.

Orlando Regional Medical Center [Online]. "Multi-Modality Pain Control for Rib Fractures" [Retrieved Jun. 6, 2013]. Retrieved from the Internet: <URL: http://www.surgicalcriticalcare.net/Guidelines/rib%20fracture%202010.pdf>. Accepted on Nov. 30, 2010. pp. 1-4.

Wu et al. "Thoracic Epidural Analgesia versus Intravenous Patient-Controlled Analgesia for the Treatment of Rib Fracture Pain after Motor Vehicle Crash". The Journal of Trauma: Injury, Infection, and Critical Care. 47(3); 1999:564-567.

U.S. Appl. No. 12/699,595, Pavliv.

U.S. Appl. No. 12/722,682, Pavliv.

*Pharmacokinetic Data*, Caldolor® (ibuprofen) Injection, Medical Information: PK, Sep. 1, 2009, Cumberland Pharmaceuticals, pp. 1-8.

Boucher, Bradley A., et al., *Pharmacokinetic Changes in Critical Illness*, Crit Care Clin 22 (2006), pp. 225-271.

Davies, Neal M., *Clinical Pharmacokinetics of Ibuprofen: The First 30 Years*, Clin Pharmacokinet Feb. 1998: 34(2) pp. 101-154.

Morris, Peter E., et al., *A multi-center, randomized, double-blind, parallel, placebo-controlled trial to evaluate the efficacy, safety, and pharmacokinetics of intravenous ibuprofen for the treatment of fever in critically ill and non-critically ill adults*, Critical Care, 2010, 14:R125, pp. 1-13.

Gordan R. Bernard, et al., *The Effect of Ibuprofen on the Physiology and Survival of Patients With Sepsis*, The New England Journal of Medicine, vol. 336, No. 13, p. 912-918 (1997).

Product Information: Caldolor™, Jun. 2009.

SCCM: *IV Ibuprofen Controls Fever in Critically Ill Patients*, Feb. 3, 2009.

JV Aranda, et al., *Pharmacokinetics and protein binding of intravenous ibuprofen in the premature newborn infant*, Acta Paediatr 86: 289-93, 1997.

Morris, Peter, et al., *A multi-center, randomized, double-blind, placebo-controlled trial of the efficacy and safety of intravenous ibuprofen in febrile adults*, Crit Care Med 2008, vol. 36, No. 12 (Suppl), p. A18, Abstract.

Grossman, et al., Pathophysiology of Cystic Fibrosis: Implication for critical care Nurses, Crit. Care Nurse, 2005, vol. 25, pp. 46-51.

(56) References Cited

OTHER PUBLICATIONS

Konstan, et al., Ibuprofen in children with cystic fibrosis; pharmacokinetics and adverse effects, J. Pediatr. Jun. 1991, vol. 116, No. 6, pp. 956-964, Abstract.
International Search Report and Written Opinion mailed on Jul. 13, 2010 issued in connection with corresponding PCT Patent Application No. PCT/US10/36015.
Office Action dated Mar. 9, 2011 issued in connection with corresponding U.S. Appl. No. 12/830,991.
Applicant's Response to Office Action dated Feb. 4, 2011 filed in connection with corresponding U.S. Appl. No. 12/830,991.
Office Action dated Nov. 10, 2010 issued in connection with corresponding U.S. Appl. No. 12/830,991.
Applicant's Response to Office Action dated Oct. 27, 2010 filed in connection with corresponding U.S. Appl. No. 12/830,991.
Office action dated Sep. 28, 2010 issued in connection with corresponding U.S. Appl. No. 12/830,991.
Applicant's Response to Office Action dated Sep. 27, 2010 filed in connection with corresponding U.S. Appl. No. 12/830,991.
Applicant's Response to Office Action dated Sep. 8, 2010 filed in connection with corresponding U.S. Appl. No. 12/830,991.
Office Action dated Aug. 9, 2010 issued in connection with corresponding U.S. Appl. No. 12/830,991.
Office Action dated Mar. 18, 2011 issued in connection with the corresponding U.S. Appl. No. 12/570,912.
Stanik-Hutt "Pain management in the critically ill", Critical Care Nurse, vol. 23, No. 2, Apr. 2003, pp. 99-103.
Hogarth et al "Management of sedation in mechanically ventilated patients", Curr. Opin. Crit. Care vol. 10, 2004, pp. 40-46.

* cited by examiner

ADMINISTRATION OF INTRAVENOUS IBUPROFEN

This application claims the benefit under 35 U.S.C. §119 (e) of U.S. Provisional Patent Application No. 61/159,585, filed Mar. 12, 2009, the entire disclosure of which is hereby incorporated herein by reference for all purposes.

FIELD OF THE INVENTION

Provided are methods for treating pain and/or reducing the need for narcotic analgesics post surgery by intravenously administering a pharmaceutical composition comprising an effective amount of 2-(4-isobutylphenyl) propionic acid.

BACKGROUND OF THE INVENTION 2-(4-isobutylphenyl) propionic acid, whose International Nonproprietary Name is ibuprofen, is a well-known anti-inflammatory drug having a molecular weight of 206.28 and the following chemical structure:

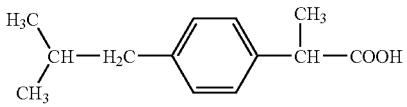

(Merck Index 12th ed., n4925, page 839). Originally patented in the 1960's, ibuprofen is now marketed generically, as well as under the tradenames of Motrin®, Advil®, and Nuprin® for the treatment of pain, inflammation, and fever. The U.S. Food and Drug Administration recently approved a new formulation of ibuprofen for intravenous administration to be marketed under the trade name Caldolor®.

Ibuprofen is readily available as the racemic mixture ((RS)-Ibuprofen) of the two enantiomers, (R)-Ibuprofen and (S)-Ibuprofen. Even though the (S) enantiomer is the biologically active form, most preparations contain the racemic mixture since the (R) enantiomer is converted to the active (S) form in-vivo. For simplicity, hereinafter the term "ibuprofen" will be used to indicate any one of the (R) enantiomer, the (S) enantiomer, or the racemate.

Ibuprofen is currently approved for use as oral treatment for minimal to moderate pain from arthritis, surgery, sunburn, menstruation, and fever. Like aspirin and other drugs in the NSAID family, ibuprofen is believed to reduce the inflammatory response by inhibiting the formation of prostaglandins. Several studies have demonstrated the success of oral or rectal ibuprofen in the reduction of fever and the subjective symptoms associated with it.

Ibuprofen is also available as an investigational intravenous preparation and has been studied in Phase 2 and Phase 3 placebo controlled trials of patients with fever and severe sepsis. In these studies, intravenous ibuprofen reduced fever and pulse rate and lessened lactic acidosis in patients with sepsis. These studies also demonstrated that ibuprofen administered intravenously was safe as determined by detailed evaluation of renal function, gastrointestinal bleeding, transfusion requirements, and other serious adverse events (SAEs). Additional clinical studies have evaluated the safety and pharmacokinetics of intravenous ibuprofen formulations given to healthy adult volunteers.

Although ibuprofen has many advantages over other analgesics such as aspirin and acetaminophen, it is very poorly soluble in water. Thus, certain dosage forms of ibuprofen, especially injectable liquids, have been difficult to develop. Several U.S. patents have addressed this problem.

For example, U.S. Pat. No. 4,309,421 appears to describe water-soluble complexes of ibuprofen and phospholipids suitable for parenteral administration. U.S. Pat. Nos. 4,859,704 and 4,861,797 appear to describe the synthesis of alkali metal salts of ibuprofen for preparing a liquid ibuprofen formulation.

Other U.S. patents appear to address this problem by preparing an ibuprofen salt with a basic amino acid as the active pharmaceutical ingredient and then solubilizing the salt to produce a liquid dosage form.

For example, U.S. Pat. No. 5,200,558 appears to describe enhanced analgesic effects of S (+) ibuprofen as salts of L and D amino acids, including arginine, in various dosage forms, including as an injectable solution. U.S. Pat. No. 4,279,926 appears to describe the use of basic amino acid salts of propionic acids for relieving pain and treating inflammatory conditions. Similarly, U.S. Pat. No. 5,463,117 appears to describe the preparation of salts of ibuprofen with basic amino acids. Finally, U.S. Pat. No. 6,005,005 appears to describe a liquid composition for oral use containing ibuprofen and arginine.

U.S. Pat. No. 6,727,286 B2 describes, among other things, a pharmaceutical composition comprising an aqueous solution of arginine and ibuprofen, wherein the molar ratio of arginine to ibuprofen is less than 1:1, as well as a method of making the same. That patent also provides a method of treating a condition chosen from pain, inflammation, fever, and/or other conditions alleviated by ibuprofen comprising administering a pharmaceutical composition comprising an aqueous solution of arginine and ibuprofen, wherein the molar ratio of arginine to ibuprofen is less than 1:1. The entire contents of U.S. Pat. No. 6,727,286 B2 are hereby incorporated herein by reference.

The U.S. Food and Drug Administration recently approved a new formulation of ibuprofen for intravenous administration to be marketed under the trade name Caldolor® by Cumberland Pharmaceuticals, Inc. Caldolor® contains the active ingredient ibuprofen. As described on the labeling for Caldolor®, "each 1 mL of solution contains 100 mg of ibuprofen in Water for Injection, USP. The product also contains 78 mg/mL arginine at a molar ratio of 0.92:1 arginine:ibuprofen. The solution pH is about 7.4." Caldolor® is sterile and is intended for intravenous administration only.

Caldolor® possesses antiinflammatory, analgesic, and antipyretic activity. As such, Caldolor® is indicated in adults for the management of mild to moderate pain and the management of moderate to severe pain as an adjunct to opioid analgesics. 400 mg to 800 mg of Caldolor® is administered intravenously every 6 hours as necessary to treat pain. Caldolor® is also indicated for the reduction of fever in adults. 400 mg of Caldolor® is administered intravenously, followed by 400 mg every 4 to 6 hours or 100-200 mg every 4 hours as necessary to treat fever.

Physicians have options in terms of pain and fever control, but each seems to come with a trade-off. It would be highly desirable to provide a new development in the management of pain and fever which improves patient care.

Prior publications report that analgesic potency may be improved while reducing undesirable effects by combining an opioid with an NSAID or an analgesic such as acetylsalicylic acid or acetaminophen, in such a way as to obtain a synergistic analgesic effect allowing for a reduction in the total dose of both the NSAID and analgesic. For example, U.S. Pat. No. 4,569,937, issued to Baker et al. on Feb. 11, 1986, describes a combination of oxycodone with ibuprofen in a ratio of oxycodone/ibuprofen from 1:6 to about 1:400. U.S. Pat. No. 4,690,927, issued to Voss et al. on Sep. 1, 1987, describes a combination of the NSAID diclofenac and codeine in a weight ratio of diclofenac to codeine of about 1:1 to about 3:1. U.S. Pat. No. 5,190,947, issued to Riess et al. on Mar. 2, 1993, describes a diclofenac-codeine salt ([2-[2,6-dichlorophenyl)-amino]-phenyl]-acetic acid). U.S. Pat. No. 4,844,907, issued to Elger et al. on Jul. 4, 1989, describes a multiphase tablet combining a narcotic analgesic phase and an NSAID phase in separate layers. U.S. Pat. No. 4,587,252, issued to Arnold et al. on May 6, 1986, describes a process for treating pain using a combination of hydrocodone and ibuprofen.

OBJECTS AND SUMMARY OF THE INVENTION

It is an object of the present invention to provide a method for the treatment of pain and/or fever in human patients which allows the patients to become ambulatory faster than typical with the use of other known agents used by those skilled in the art.

It is another object of the invention to provide a treatment for pain and/or fever which has an excellent safety profile.

It is another object of the invention to provide a method of treating human patients who are being treated with opioid analgesics in a manner which reduces opioid side effects.

It is another object of the invention to provide a method of treating human patients who are being treated with opioid analgesics which is opioid sparing.

It is another object of the invention to provide a method of treating patients experiencing mild to severe pain and fever, via the administration of an intravenous dose of ibuprofen.

It is another object of the invention to provide a method of treating patients experiencing mild to severe pain which results in a reduction in pain intensity, e.g., as measured by visual analog scores.

In accordance with the above objects and others, the present invention is directed in part to the administration of intravenous ibuprofen to human patients either prior to, during, or after surgery.

The invention is further directed to a method for reducing pain in human patients undergoing surgical procedures, comprising intravenously administering ibuprofen pre-surgically to the patient in an amount effective to significantly reduce post-operative pain in the patients. In some instances, the administration of ibuprofen in this manner can reduce pain without the need for the administration of an opioid analgesic and/or delay the time to need morphine for the patients.

The invention is also directed in part to the administration of intravenous ibuprofen to patients who are being treated with an opioid analgesic(s) for pain, and thereby providing an opioid-sparing effect, enabling the reduction of the dose of opioid to the patient. The administration of intravenous ibuprofen in such situations further provides a reduction in side effects associated with the administration of opioid analgesics. Further, the administration of intravenous ibuprofen has been found to reduce pain scores (e.g., VAS scores) in patients who are concurrently administered opioid analgesics, as compared to patients receiving opioid analgesics alone.

In further embodiments, the invention is directed in part to a method of treating human patients for pain associated with a surgical procedure, comprising administering an effective dose of intravenous ibuprofen prior to surgery.

Further embodiments of the invention entail administering an effective dose of intravenous ibuprofen prior to the start of surgery on the patient, thereafter performing surgery on the patient, and thereafter administering an effective dose of an opioid analgesic to the patient such that the patient experiences relief from pain associated with the surgery, the dose of opioid analgesic being lower than the dose of the opioid analgesic necessary to provide the same level of pain relief if the intravenous ibuprofen is not administered.

In further embodiments, the administration of intravenous ibuprofen in the surgical setting allows the patient to become ambulatory post-surgery at an earlier time point than if the intravenous ibuprofen is not administered.

In further embodiments, the method comprises intravenously administering the effective dose of ibuprofen to a patient prior to the start of surgery at the onset of anesthesia.

Further embodiments of the invention are directed to a method of treating pain in human patients prior to the start of surgery via the administration of about 800 mg intravenous ibuprofen administered every 6 hours starting with the onset of anesthesia.

In certain preferred embodiments, the patients are undergoing orthopedic surgery.

In additional embodiments, the invention is directed to a method of reducing surgical pain in human patients, comprising administering an effective dose (e.g., about 800 mg) of intravenous ibuprofen prior to the start of surgery on the patient, thereafter performing surgery on the patient, and thereafter administering an effective dose of an opioid analgesic to the patient such that the patient experiences relief from pain associated with the surgery. In preferred embodiments, the method further comprises intravenously administering an 800 mg dose of ibuprofen every six hours post-operatively to the patient. Preferably, the intravenous ibuprofen and opioid therapy is continued until the patient no longer is suffering from post-operative pain.

In certain preferred embodiments, the human patients receiving 800 mg intravenous ibuprofen as described herein experience a significant reduction in pain as measured, e.g., by the VAS-AUC with movement for the post-operative period (hours 6-28 after completion of the surgical procedure).

In certain preferred embodiments, the human patients receiving the dose of ibuprofen as described herein require the administration of less opioid analgesic (e.g., morphine) than the dose of opioid typically required to provide an equivalent level of pain relief without the administration of intravenous ibuprofen.

In certain preferred embodiments, the human patients receiving the dose of ibuprofen as described herein experience a significant reduction in pain as measured by the VAS at rest area under the curve and by the VRS for the post-operative period (hours 6-28 after completion of the surgical procedure).

In certain preferred embodiments, the human patients experience less pain via the intravenous administration of ibuprofen as compared to typical patients undergoing the same procedure without the benefit of the intravenous administration of ibuprofen.

In preferred embodiments, the human patients receiving the intravenous dose(s) of ibuprofen used significantly less opioid analgesic. In certain preferred embodiments, the human patients receiving intravenous ibuprofen experience about a 30% reduction in mean morphine consumption.

The invention is further directed to a safe and effective method for management of pain associated with orthopedic surgical procedures in human patients, comprising intravenously administering an 800 mg dose of ibuprofen pre-surgically to the patient. In preferred embodiments, the method further comprises intravenously administering an 800 mg dose of ibuprofen every six hours post-operatively to the patient. In further embodiments, one or more opioid analgesics are administered to the human patient post-operatively, preferably, in an amount (of opioid analgesic) that is less than that typically required to control pain in human patients (due to the co-administration of intravenous ibuprofen).

The invention is further directed to a safe and effective method for reducing the amount of opioid analgesic administered to human patients undergoing orthopedic surgical procedures, comprising intravenously administering an 800 mg dose of ibuprofen pre-surgically to the patient. In preferred embodiments, the method further comprises intravenously administering an 800 mg dose of ibuprofen every six hours post-operatively to the patient. In further embodiments, one or more opioid analgesics are administered to the human patient post-operatively, preferably, in an amount (of opioid analgesic) that is less than that typically required to control pain in human patients (due to the co-administration of intravenous ibuprofen).

The invention is further directed to method for improving the time to ambulation post-operatively in human patients undergoing orthopedic surgical procedures, comprising intravenously administering ibuprofen pre-surgically to the patient in an amount effective to improve the time to ambulation. In preferred embodiments, the dose of ibuprofen administered intravenously is from about 400 mg to about 800 mg. In preferred embodiments, the method further comprises intravenously administering the dose of ibuprofen every six hours post-operatively to the patient. In further embodiments, one or more opioid analgesics are administered to the human patient post-operatively, preferably, in an amount (of opioid analgesic) that is less than that typically required to control pain in human patients (due to the co-administration of intravenous ibuprofen).

In preferred embodiments of the invention, there is a reduction in the use of opioid analgesic (e.g., morphine) through 24 hours in patients receiving 800 mg ibuprofen. In certain embodiments, there is at least a 25 percent reduction in median morphine consumption in patients receiving 800 mg ibuprofen as compared to placebo. In certain preferred embodiments, there is at least a 30 percent reduction in median opioid consumption in patients, and in certain further preferred embodiments, there is a at least a 40 percent reduction in median opioid consumption in patients.

In preferred embodiments, patients receiving both 400 mg and 800 mg ibuprofen intravenously experience a significant reduction in pain as measured by the VAS with movement and at rest area under the curve for the first 24 hours, from 6 through 24 hours, and from 12 through 24 hours after surgery and a reduction in pain as measured by the VAS at rest area under the curve for the first 24 hours, from 6 through 24 hours, and from 12 through 24 hours.

Accordingly, the invention is further directed to a method for reducing pain in human patients undergoing orthopedic surgical procedures with the administration of an opioid analgesic, comprising intravenously administering ibuprofen pre-surgically to the patient in an amount effective to significantly reduce post-operative pain in the patients, as measured by the VAS with movement and at rest area under the curve for the first 24 hours.

DETAILED DESCRIPTION OF THE INVENTION

NSAIDs are effective adjuncts to opioid analgesia for moderate to severe pain, resulting in pain relief and opioid dose sparing. NSAIDs alone could provide effective analgesia post-surgery when mild to moderate pain is expected. There is also evidence that, by avoiding or decreasing opioid use, NSAIDs can reduce the incidence of opioid associated adverse events.

In some embodiments of the present invention, intravenous ibuprofen is administered to a patient for the treatment of post-operative pain as measured by reduction in the requirement for the narcotic analgesic, morphine, post surgery. Patients who may be administered an intravenous ibuprofen dose include those scheduled for elective single site surgery with anticipated need for post-operative I.V. morphine analgesia with anticipated use of >24 hours having adequate IV access. Examples of types of surgeries include orthopedic surgery (knee, hip or shoulder joint replacement or reconstruction), gynecologic including hysterectomy, major abdominal surgery including gall bladder, bowel or lower abdominal general investigative surgery (dual site bone graft orthopedic procedures qualify for inclusion). The dose of the intravenous ibuprofen can be from about 400 mg to about 800 mg, with dosing in certain embodiments occurring over a 30 minute interval of time every 6 hours. The post surgery dose of intravenous ibuprofen can be administered for up to 8 doses or can continue further on an every 6 hour or as needed basis.

Certain methods described herein comprise administering to a post surgical patient an intravenous pharmaceutical composition comprising ibuprofen. Intravenous pharmaceutical compositions of ibuprofen include any formulation suitable for administration to a patient via any intravenous method, including a bolus. In some embodiments the rate of infusion is such that the dose is administered over a period of about 30 minutes. In some embodiments the rate of infusion is such that the dose is administered over a period of less than 30 minutes. In some embodiments the rate of infusion is such that the dose is administered over a period of greater than 30 minutes.

In alternative embodiments of the treatment methods described herein a pharmaceutical formulation comprising ibuprofen is administered to a patient via an injection method. In such embodiments the pharmaceutical formulation of ibuprofen is a formulation suitable for administration to a patient via the injection method. Suitable injection methods include, in addition to intravenous injection, intraarterial infusion, intramuscular injection, transdermal injection, and subcutaneous injection.

Suitable carriers for intravenous administration include physiological saline or phosphate buffered saline (PBS), and solutions containing solubilizing agents, such as glucose, polyethylene glycol, and polypropylene glycol and mixtures thereof.

The formulation may include an aqueous vehicle. Aqueous vehicles include, by way of example and without limitation, Sodium Chloride Injection, Ringers Injection, Isotonic Dextrose Injection, Sterile Water Injection, Dextrose, and Lactated Ringers Injection. Nonaqueous parenteral vehicles include, by way of example and without limitation, fixed oils of vegetable origin, cottonseed oil, corn oil, sesame oil and peanut oil. Antimicrobial agents in bacteriostatic or fungistatic concentrations must be added to parenteral preparations packaged in multiple dose containers which include phenols or cresols, mercurials, benzyl alcohol, chlorobutanol, methyl and propyl p hydroxybenzoic acid esters, thimerosal, benzalkonium chloride and benzethonium chloride. Isotonic agents include, by way of example and without limitation, sodium chloride and dextrose. Buffers include phosphate and citrate. Antioxidants include sodium bisulfate. Local anesthetics include procaine hydrochloride. Suspending and dispersing agents include sodium carboxymethylceluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include, by way of example and without limitation, ethyl alcohol, polyethylene glycol and propylene glycol for water miscible vehicles and sodium hydroxide, hydrochloric acid, citric acid or lactic acid for pH adjustment.

Typically a therapeutically effective dosage is formulated to contain a concentration of at least about 0.1% w/w up to about 90% w/w or more, such as more than 1% w/w of ibuprofen.

As used herein a "dosage regimen" refers to the protocol used to administer an intravenous pharmaceutical formulation comprising ibuprofen to a patient. In some embodiments the dosage regimen comprises a dose amount and dosing interval. In some embodiments the dosage regimen further comprises a dosing duration. As used herein "dosing duration" refers to the period of time over which a dose is administered. For example, if a volume of pharmaceutical composition comprising 400 mg of ibuprofen is administered over a dosing duration of 30 min and administration of a dose is initiated every 6 hours, then the dosage regimen is 400 mg, every six hours, administered over 30 minutes. In some embodiments the dosage duration is defined simply as 400 mg, every six hours.

In some embodiments described herein a dosage regimen for post surgical patients is defined as one that results in decreased usage of narcotic analgesic and/or decreased perception of pain and decreased side effects from use of a narcotic analgesic.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The invention is further directed to a method of treating at post surgical patient in need of pain relief comprising administering to the patient an intravenous pharmaceutical composition comprising ibuprofen at a dosage of (i) 400 mg ibuprofen or (ii) 800 mg ibuprofen. In certain preferred embodiments of this method, the dose of ibuprofen produces a decreased need for narcotic analgesic, decreased side effects from use of a narcotic analgesic and/or decreased perception of pain.

Several prescription and nonprescription brands of ibuprofen are approved for the treatment of fever, pain, and other indications. The recommended over the counter, single dose of oral ibuprofen to treat mild to moderate pain in adults is 400 mg every 4 to 6 hours. For chronic indications, such as rheumatoid arthritis and osteoarthritis, up to 3200 mg/day may be administered (300 mg qid, or 400/600/800 mg tid or qid).

The intravenous ibuprofen formulation of the present invention are the first and only intravenous formulation of ibuprofen available to treat mild to severe pain in adults and to reduce fever in children and adults. Oral ibuprofen has been available for more than 30 years and has an excellent record of efficacy and safety. The intravenous formulation is now commercially available in the U.S. 4-mL and 8-mL vials (each 100 mg/mL) for dilution in either saline or dextrose solution.

Examples of suitable IV ibuprofen treatments in accordance with the invention include the following: for simple adult dosing for pain: 800 mg every 6 hours. For simple adult dosing for fever: 400 mg every 4 to 6 hours. Critically ill patients may require higher doses for fever management. In addition, even in critically ill patients the dose may be adjusted up to 800 mg, not to exceed 3200 mg total daily dose. Intuitive pediatric fever dosing: 10-15 mg/kg up to 400 mg per single dose every 4 hours, consistent with pediatric oral dosing. The dose can be administered, e.g., via a 5-to-10-minute IV infusion.

As described herein, in clinical trials the intravenous ibuprofen when administered to human patients significantly reduced postoperative pain, measured at rest and with movement, and has a clinically significant opioid-sparing effect. There were significantly fewer patients in the IV ibuprofen treatment group with at least one morphine side effect compared with placebo patients. The intravenous ibuprofen was also highly effective in reducing fever in hospitalized patients. No bleeding or renal toxicity was reported in the clinical studies with intravenous ibuprofen.

As demonstrated, e.g., by the clinical studies detailed in the appended examples, intravenous ibuprofen used in accordance with the invention provides a treatment for pain and/or fever using the intravenous route of administration, and is useful for the treatment of mild to severe pain and the reduction of fever in adults and children under 12 years of age. Intravenous ibuprofen used in accordance with the methods of the invention provides pain control, e.g., for abdominal and orthopedic surgical procedures; effective fever reduction, even in critically ill patients; is opioid sparing when used for post-operative pain; provides a reduction in opioid side effects; allows patients to become ambulatory faster; and has an excellent safety profile.

The use of intravenous ibuprofen formulations in accordance with the present invention provide, e.g., the following benefits: speed relief of pain and/or fever to expedite release from a hospital or hospital-like setting; IV ibuprofen speeds relief to expedite hospital release, as demonstrated by a fast reduction of mild to severe pain and fever in adults and fever in children under 12 years of age; a reduction in pain at rest and with movement as measured by visual analog scores (VAS) following abdominal and orthopedic surgeries; a reduction in opioid side effects (nausea, vomiting, constipation); does not cause bleeding or renal concerns observed in clinical trials; and provides an improvement in time to ambulation may enable facilities to schedule additional procedures in the ambulatory setting.

Pain control in the postoperative setting and fever in critical care can be major concerns. Currently there is nothing available in an IV to control fever. Hospital/ambulatory care centers want to get patients on their feet and released sooner, but some pain control options have side effects and safety issues that can lengthen the hospital stay. Controlling pain is a challenge. Physicians are well aware of the JCAHO guidelines and are concerned about doing more to control pain. Dosing limitations of some agents make the task even more daunting, and opioid side effects make patients feel less like themselves. Physicians know and trust ibuprofen to control pain and fever. However, prior to the introduction of Caldolor®, ibuprofen was only available in an oral formulation and its use is limited in the hospital/ambulatory care setting.

With respect to the reduction of pain, as detailed in the appended examples describing the clinical use of IV ibuprofen, treatment with IV Ibuprofen and morphine significantly reduced pain at rest and with movement 24 hours post⁻ surgery versus patients on only morphine delivered via PCA.— In addition to a morphine sparing effect IV Ibuprofen provided a 20% reduction in pain vs morphine PCA alone in abdominal and orthopedic procedures (P=0.003) (at rest AUC of visual analog score). In addition to a morphine sparing effect, IV Ibuprofen provided a 21% reduction in pain vs morphine PCA alone in abdominal hysterectomy patients (P=0.003)(at rest AUC of visual analog score). From hour 9 up to 24 hours after surgery, significantly less pain was still reported by patients on IV Ibuprofen vs morphine PCA alone (P<0.027). Also, IV Ibuprofen significantly improved time to ambulation vs placebo (P-0.009) Patients reported less pain at rest and with movement when IV ibuprofen was initiated intra-operatively −24 hours postsurgery vs placebo (P=0.003); −48 hours postsurgery vs placebo (P<0.040).

With respect to its opioid sparing capabilities, the administration of IV ibuprofen provides significant opioid-sparing pain reduction in orthopedic and abdominal procedures. IV Ibuprofen provides effective pain relief with fewer opioid side effects. A significant reduction in opioid use was reported after abdominal and orthopedic procedures vs patients on morphine delivered via PCA (P-0.030). A 26% reduction in median morphine consumption was reported in abdominal/orthopedic procedures within first 24 hours post ¬ surgery. A significant reduction in opioid use was reported after abdominal hysterectomy vs patients on morphine delivered via PCA (P<0.001), with a 21% reduction in median morphine consumption in abdominal hysterectomy procedures within first 24 hours post-surgery.

With respect to intravenous ibuprofen administered in accordance with the invention for fever, the results of a phase 3 clinical trial demonstrated that within 4 hours, 77% of patients had significant fever reduction vs 32% with placebo. The observed treatment effect remained throughout dosing (P=0.0005). Rapid fever reduction was seen as fast as 30 minutes, e.g., in malaria patients as detailed in the appended example. Significant reduction in temperature was maintained over 48-hour study period in critically ill patients (P=0.05). 100% of IV Ibuprofen treated patients had reduced fever at 4 hours. Nearly 4 times as many placebo-treated patients as IV Ibuprofen treated patients had uncontrolled fever at 24 hours.

In another aspect of the invention, critically ill patients also receive acetaminophen first to treat fever. Patients who were in the active IV ibuprofen arm subsequently required less acetaminophen and had better fever control than in the arm with acetaminophen alone, based on a subset analysis. IV ibuprofen offers physicians another option to treat ICU and non-ICU patients who cannot tolerate oral fever preparations.

With respect to safety, in all clinical studies conducted to date, IV Ibuprofen had no impact on key metabolic and hematologic parameters. Creatinine levels, hematocrit or requirements for transfusion were similar to placebo. Mean platelet count remained in the normal range. No postoperative GI bleeding or renal complications were seen in up to 5 days of IV Ibuprofen treatment (includes abdominal and orthopedic surgical procedures). In all clinical trials, bleeding and renal dysfunction were comparable to placebo. IV Ibuprofen was shown to be safe and well tolerated in the critically ill hospitalized patient population. The adverse event profile for IV ibuprofen was comparable to placebo.

Studies have shown that multimodal analgesic techniques can enhance recovery and patient outcome after ambulatory procedures, improving hospital throughput. For purposes of the present invention, multimodal refers to "balanced" analgesia. In other words, more than one modality of pain control can be used in order to obtain beneficial analgesic effect while reducing opioid-related side effects. Meta-analyses of NSAIDs (including ibuprofen) have shown robust effects on analgesia and/or opioid dose sparing, with corresponding reduction in opioid side effects.

The present invention is directed in part to a method for reducing pain in human patients undergoing surgical procedures with the administration of an opioid analgesic, comprising intravenously administering ibuprofen pre-surgically to the patient in an amount effective to significantly reduce post-operative pain in the patients, as measured by the VAS with movement and at rest area under the curve for the first 24 hours. In certain embodiments, the method further comprises the step of intravenously administering a dose of ibuprofen every six hours post-operatively to the patient for at least 24 hours post-operatively. In certain embodiments, the method comprises intravenously administering an effective dose of ibuprofen prior to surgery. The dose of ibuprofen is from preferably from about 400 mg to about 800 mg.

A further aspect of the invention comprises administering one or more opioid analgesics to the human patients post-operatively. Preferably, the one or more opioid analgesics in an amount that is less than that typically required to control pain in human patients having undergone the same surgical procedure. In other words, intravenously administering the intravenous ibuprofen to patients in a sufficient dose provides an opioid-sparing effect, enabling the reduction of the dose of opioid to the patients. In such embodiments, the dose of ibuprofen is about 800 mg. Preferably, the human patients receiving intravenous ibuprofen experience at least a 20% reduction, or a 25% reduction, or at least a 30% reduction, or at least a 40% reduction in mean morphine consumption.

In further embodiments, the method further comprises intravenously administering the intravenous ibuprofen in a sufficient dose to provide a reduction in side effects associated with the administration of opioid analgesics.

In yet further embodiments, the method further comprises intravenously administering the intravenous ibuprofen in a sufficient dose to reduce pain scores in patients who are concurrently administered opioid analgesics, as compared to patients receiving opioid analgesics alone.

In certain preferred embodiments, the invention comprises intravenously administering the ibuprofen in a sufficient dose such that the patients become ambulatory post-surgery at an earlier time point than if the intravenous ibuprofen is not administered.

In certain embodiments, the invention further comprises intravenously administering to the patient a dose of ibuprofen selected from 400 mg and 800 mg, such that the patient experiences a significant reduction in pain as measured by the VAS with movement and/or the VAS at rest area under the curve for time points within the first 24 hours after surgery. In certain preferred embodiments, the time points are from 0 through 24 hours, and from 6 through 24 hours, and from 12 through 24 hours after surgery.

In certain preferred embodiments of the invention, the ibuprofen is intravenously administered every 6 hours starting with the onset of anesthesia.

The invention is further directed to a method of reducing surgical pain in human patients, comprising intravenously administering about 800 mg of ibuprofen prior to the start of surgery on the patients, administering an effective dose of an opioid analgesic to the patient such that the patient experiences relief from pain associated with the surgery, the effective dose being an amount that is less than that typically required to control pain in human patients having undergone the same surgical procedure; and intravenously administering a further dose of 800 mg dose of ibuprofen every six hours post-operatively to the patient at least until 24 hours after surgery.

In preferred embodiments, the intravenous ibuprofen provides an opioid-sparing effect, enabling the reduction of the dose of opioid to the patients. Preferably, the human patients receiving intravenous ibuprofen experience at least a 20% reduction, or a 25% reduction, or at least a 30% reduction, or at least a 40% reduction in mean morphine consumption.

The invention is further directed to a method for improving the time to ambulation post-operatively in human patients undergoing orthopedic surgical procedures, comprising intravenously administering ibuprofen every 6 hours starting with the onset of anesthesia intravenously at least until 24 hours after surgery in an amount effective to improve the time to ambulation. Preferably, the dose of ibuprofen is from about 400 mg to about 800 mg. Preferably, this embodiment further comprises administering at least one opioid analgesic to the human patients post-operatively in an amount that is less than that typically required to control pain in human patients who have undergone the same surgical procedure.

The opioids are a group of drugs, both natural and synthetic, that are employed primarily as centrally-acting analgesics and are opium or morphine-like in their properties. The opioids include morphine and morphine-like homologs, including, e.g., the semisynthetic derivatives codeine (methylmorphine) and hydrocodone (dihydrocodeinone) among many other such derivatives. Morphine and related opioids exhibit agonist activity at central nervous system or CNS (referring to the brain and spinal cord) mu opioid receptors as well as showing affinity for the delta and kappa opioid receptors, to produce a range of effects including analgesia, drowsiness, changes in mood and mental clouding. In addition to potent analgesic effects, the morphine-related opioids may also cause a number of undesirable effects, including, for example, respiratory depression, nausea, vomiting, dizziness, mental clouding, dysphoria, pruritus, constipation, increased biliary tract pressure, urinary retention and hypotension.

Although morphine was used as the opioid analgesic in the studies reported in Examples 1-3, one skilled in the art will recognize that other opioid analgesics can be used instead of part or all of the morphine. Opioid analgesics which may be used in accordance with the invention include, but are not limited to, alfentanil, allylprodine, alphaprodine, anileridine, benzylmorphine, bezitramide, buprenorphine, butorphanol, clonitazene, cyclazocine, desomorphine, dextromoramide, dezocine, diampromide, diamorphone, dihydrocodeine, dihydromorphine, dimenoxadol, dimepheptanol, dimethylthiambutene, dioxaphetylbutyrate, dipipanone, eptazocine, ethoheptazine, ethylmethylthiambutene, ethylmorphine, etonitazene, fentanyl, heroin, hydromorphone, hydroxypethidine, isomethadone, ketobemidone, levallorphan, levorphanol, levophen-acylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, salts thereof, complexes thereof; mixtures of any of the foregoing, mixed mu-agonists/antagonists, mu-antagonist combinations salts or complexes thereof, and the like. In certain preferred embodiments, the opioid analgesic is a mu or kappa opioid agonist. In certain preferred embodiments, the opioid analgesic is morphine, dihydrocodeine, hydromorphone, fentanyl, oxycodone, oxymorphone, salts thereof, and mixtures of any of the foregoing.

DETAILED DESCRIPTION OF PREFERRED EMBODIMENTS

The following example represents specific embodiments of the foregoing discovery, and is not representative of the entire scope of the invention.

Example 1

Example 1 was a randomized, double-blind, placebo controlled study to evaluate treatment of pain in post-operative adult patients. The primary objective of this study was to determine the efficacy of intravenous ibuprofen compared to placebo for the treatment of post-operative pain as measured by reduction in the requirement for the narcotic analgesic, morphine, post surgery. Secondary objectives were 1) to determine the optimal dose of ibuprofen for post-operative pain treatment; 2) to determine the efficacy of ibuprofen compared to placebo for the treatment of post-operative pain as determined by patient's self assessment of pain; 3) to determine the safety of ibuprofen compared to placebo for the treatment of post-operative pain; and 4) to determine whether the use of ibuprofen reduces the incidence of opioid related side effects.

A total of 406 participants were randomized into one of 3 groups, with two groups receiving different doses of ibuprofen and the third group receiving a placebo reference product. The test product dose and mode of administration was intravenous ibuprofen: 400 mg or 800 mg, intravenous. The reference product, dose and mode of administration was normal saline, 100 ml, intravenous. Saline was chosen as the control group (placebo) for this study, to ensure blinding and allow for analysis of treatment effect. The duration of treatment was up to 5 days post surgery. The dosing was one dose every 6 hours for 8 doses, then as needed for pain every 6 hours for up to 5 days post surgery. Groups were stratified according to two age groups: <45 and >45 to 70 years of age and two weight groups: <75 kg and >75 kg of weight.

The study participants were randomized based on criteria for an efficacy evaluable population (EEP) versus an intent to treat population (ITT). The ITT included all patients who were randomized and received at least a partial dose of ibuprofen. Patients included in the ITT who had no major protocol violations with regard to inclusion or exclusion criteria or study conduct and had all primary efficacy assessments were eligible for inclusion in the EEP: specifically, these were patients included in the ITT who received at least the first four doses of ibuprofen administered within +60 minutes of the scheduled administration time.

Eligible patients were randomized to one of the three treatment groups. All patients were able (but were not required) to receive morphine until approximately 45 minutes before the end of the surgical procedure. After that time, only fentanyl was allowed until the end of the operation. The first dose of ibuprofen was administered at approximately the initiation of skin closure. Upon discharge from the operating room, patients had access to morphine (approximately 1-2 mg q 5 minutes) upon patient request or delivered by patient-controlled analgesia (PCA). Seven subsequent doses of ibuprofen were administered intravenously over 30 minutes every 6 hours over the next two days under the protocol, for a total of 8 doses. Dosing was discontinued after 24 hours (4 doses) for certain patients due to 1) ability to tolerate oral pain medication; 2) resolution of pain; 3) no IV access; or 4) discharge from the hospital. For patients that received 8 scheduled doses of ibuprofen, additional ibuprofen could be administered as needed for pain every 6 hours through 5 days post surgery.

Other than ibuprofen or placebo, only morphine was administered for pain. Upon discharge from the operating room, patients had access to 1 mg morphine every 5 minutes upon request or by patient-controlled analgesia (PCA). If adequate pain control was not achieved the dose of morphine could have been increased to 2 mg morphine every 5 minutes. Additional morphine could be administered at the discretion of the treating physician if adequate pain control had still not been achieved. Patients given non-morphine analgesics were classified as treatment failures. Treatment failures were not replaced.

Patients were evaluated and compared for morphine requirements between the active doses and placebo using analysis of variance and covariance procedures at an overall alpha level of 0.05. Secondary efficacy parameters were also evaluated and compared among the treatment groups using appropriate statistical methods described in the statistical analysis section of the protocol. Safety information was compared between the treatment groups using Chi-Square or Cochran-Mantel-Haenszel test. Demographic, background and baseline information among the treatment groups was also described.

In determining optimal dose, a comparison of the 400 mg and 800 mg doses of ibuprofen versus placebo as measured by a reduction in the requirement for the narcotic analgesic, morphine, in the 24 hours post surgery was to be performed. Dose selection was to be based on statistical significance of $p \leq 0.05$ when comparing ibuprofen treatment versus placebo (efficacy). When comparing 400 mg ibuprofen to 800 mg ibuprofen dose selection based on efficacy criteria, it was to be based on statistical significance of $p \leq 0.10$. If efficacy was demonstrated when ibuprofen is compared to placebo, but no statistically significant difference is seen between 400 mg and 800 mg doses, the lower dose of 400 mg would be selected for the study of Example 2. If significant safety concerns were evident with the 800 mg dose and not observed with the 400 mg dose, the 400 mg dose would be selected for the study of Example 2 even if the 800 mg dose was shown to be more effective than the 400 mg dose. The optimal dose selected from this Example 1 study (400 mg or 800 mg) was then compared with placebo in the study in Example 2 with respect to morphine requirements to evaluate efficacy and safety.

The primary endpoint for the study of Example 1 was reduction in the requirement for morphine use in the 24 hours following surgery as measured by total morphine usage compared to placebo. Analysis of variance and covariance procedures were to be used to compare the reduction in the requirement for morphine use in the 24 hours following surgery among the treatment groups. Dunnet's test was to be used as a multiple comparison test to compare active dose groups with the placebo group at an overall alpha level of 0.05. Comparison of morphine use among active doses of ibuprofen was to be made using an alpha level of 0.10 to declare significance.

The primary efficacy measure was reduction in the requirement for morphine use in the 24 hours following surgery. Secondary efficacy endpoints were: (1) reduced pain intensity as measured by the patient's self-assessment of pain intensity as reported by a visual analog scale (VAS) of 0-10 with 0 being no pain and 10 being intense pain; (2) time to first subsequent narcotic analgesia for breakthrough pain; (3) nocturnal awakenings due to pain; (4) determining whether the addition of ibuprofen reduced the incidence of opioid related side-effects including time to GI motility as measured by return of bowel sounds, flatulence or bowel activity, a combined safety assessment (occurrence of diffuse pruritus, overt respiratory depression, need for post-operative urinary indwelling catheter, incidence of post-operative vomiting or need for anti-emetic medication, Richmond Agitation Sedation Scale <-3); (5) resumption of ambulation; (6) resumption of liquid intake and solid diet, and (7) length of hospital stay.

Efficacy analyses were performed on the Intent to Treat (ITT) population and the Efficacy Evaluable Population (EEP). In addition a subset of EEP patients who underwent abdominal hysterectomies (AH) were analyzed separately to evaluate efficacy in a more homogenous population.

As shown in Table 24 below, a statistically significant and clinically meaningful reduction of up to 25.6% in the EEP and 21.6% in the ITT in the use of morphine in the 24 hours following surgery was seen in the patients receiving 800 mg ibuprofen when compared to placebo. When assessing the effect in a more homogeneous population of similar surgeries (abdominal hysterectomies), the reduction in morphine was 16% in the 400 mg ibuprofen group and 41% in the 800 mg ibuprofen group.

TABLE 1

Primary Efficacy Variable: Morphine Usage in the 24 Hours Following Surgery

| | | Placebo | 400 mg IVIb | 800 mg IVIb |
|---|---|---|---|---|
| ITT | N | 134 | 134 | 138 |
| | Median | 45.25 | 44.00 | 35.50 |
| | % Reduction vs. PBO | — | 2.76% | 21.55% |
| EEP | N | 115 | 111 | 116 |
| | Median | 45.00 | 43.00 | 33.50 |
| | % Reduction vs. PBO | — | 4.44% | 25.56% |
| AH | N | 58 | 50 | 53 |
| | Median | 53.50 | 45.00 | 31.50 |
| | % Reduction vs. PBO | — | 15.89% | 41.12% |

Pain was measured by the patient's self-assessment using a Visual Analog Scale (VAS) from 0-10 with 0 being no pain and 10 being intense pain. This was measured both at rest and with movement. VAS assessments at rest and movement were taken at hours 1, 2, 3, 6, 9, 12, 15, 18, 24, 27, 30, 33, 36, 39, 42, 45, 48 and daily through day 5. Because the protocol did not require patients to be awakened to obtain pain assessments, missing pain assessments were anticipated. To account for the missing pain assessments, two missing value approaches as described in the statistical analysis plan were used to impute values. To determine the difference in overall pain at differing time-points, the area under the VAS pain curve during the first 24 hours, between 6 and 24 hours and between 12 and 24 hours were analyzed.

In the ITT population, patients receiving the 800 mg ibuprofen dose experienced significantly less pain from study hour 9 through 48 (with the exception of the 39-hour time-point) when compared with morphine only (placebo) in addition to using less morphine. Patients receiving the 400 mg ibuprofen dose also experienced less pain from study hour 9 through 48 (with the exception of the 12, 24, 27 and 33-hour time-points) when compared with morphine only (placebo). The VAS with movement AUC over 24 ($p=0.004$), from 6 through 24 ($p<0.001$) and from 12 through 24 ($p<0.001$) hours was lower in the patients receiving 800 mg ibuprofen compared to patients receiving morphine only (placebo). The VAS with movement AUC over 24 ($p=0.033$), from 6 through 24 ($p=0.008$) and from 12 through 24 ($p=0.006$) hours was lower in the patients receiving 400 mg ibuprofen compared to patients receiving morphine only (placebo). The percent pain reduction is presented below.

TABLE 2

Secondary Efficacy Variable, VAS Score measured with Movement, Median Score and % Reduction vs Placebo, ITT*

| Study Hour | Placebo N = 134 (median) | 400 mg IVIb; N = 134 (median) | % Reduction vs Placebo | 800 mg IVIb; N = 138 (median) | % Reduction vs Placebo |
|---|---|---|---|---|---|
| 1-Hour | 8.0 | 7.5 | 6.2 | 7.3 | 8.8 |
| 2-Hour | 7.3 | 7.4 | −1.4 | 6.8 | 6.8 |
| 3-Hour | 6.3 | 6.3 | 0.0 | 6.0 | 4.8 |
| 6-Hour[†] | 5.7 | 5.7 | 0.0 | 5.3 | 7.0 |
| 9-Hour | 5.2 | 4.7 | 9.6 | 4.6 | 11.5 |
| 12-Hour[†] | 5.0 | 4.5 | 10.0 | 4.3 | 14.0 |
| 15-Hour | 5.0 | 3.9 | 22.0 | 4.2 | 16.0 |
| 18-Hour[†] | 5.0 | 4.3 | 14.0 | 4.0 | 20.0 |
| 21-Hour | 4.9 | 4.1 | 16.3 | 3.8 | 22.4 |
| 24-Hour[†] | 4.5 | 4.6 | −2.2 | 3.7 | 17.8 |
| 27-Hour | 4.4 | 4.6 | −4.5 | 3.6 | 18.2 |
| 30-Hour[†] | 4.0 | 4.0 | 0.0 | 3.5 | 12.5 |
| 33-Hour | 3.8 | 3.8 | 0.0 | 3.5 | 7.9 |
| 36-Hour[†] | 4.0 | 3.6 | 10.0 | 3.5 | 12.5 |
| 39-Hour | 3.5 | 3.1 | 11.4 | 3.7 | −5.7 |
| 42-Hour[†] | 3.4 | 3.3 | 2.9 | 3.3 | 2.9 |
| 45-Hour | 3.1 | 3.3 | −6.5 | 2.7 | 12.9 |
| 48-Hour[†] | 2.3 | 3.2 | −39.1 | 2.1 | 8.7 |
| AUC_1-24 Hour | 124.8 | 113.1 | 9.4 | 107.5 | 13.9 |
| AUC_6-24 Hour | 91.5 | 80.0 | 12.6 | 76.2 | 16.7 |
| AUC_12-24 Hour | 59.1 | 50.7 | 14.2 | 47.9 | 19.0 |

*Imputation method 1 is summarized.
[†]End of dose interval, assessment just prior to next scheduled dose.

In the EEP population, patients receiving the 800 mg ibuprofen dose experienced significantly less pain from study hour 9 through 24 when compared with morphine only (placebo) in addition to using less morphine. Patients receiving the 400 mg ibuprofen dose also experienced significantly less pain from study hour 9 through 24 (with the exception of the 12-hour time-point, p<0.10) when compared with morphine only (placebo). The VAS with movement AUC over 24 (p=0.090), from 6 through 24 (p=0.015) and from 12 through 24 (p=0.005) hours was lower in the patients receiving 800 mg ibuprofen compared to patients receiving morphine only (placebo). The VAS with movement AUC over 24 (p=0.218), from 6 through 24 (p=0.064) and from 12 through 24 (p=0.035) hours was lower in the patients receiving 400 mg ibuprofen compared to patients receiving morphine only (placebo). The percent pain reduction is presented below.

TABLE 3

Secondary Efficacy Variable, VAS Score measured with Movement, Median Score and % Reduction vs Placebo, EEP*

| Study Hour | Placebo N = 115 (median) | 400 mg IVIb; N = 111 (median) | % Reduction vs Placebo | 800 mg IVIb; N = 116 (median) | % Reduction vs Placebo |
|---|---|---|---|---|---|
| 1-Hour | 8.0 | 7.5 | 6.2 | 7.8 | 2.5 |
| 2-Hour | 7.1 | 7.2 | −1.4 | 7.0 | 1.4 |
| 3-Hour | 6.0 | 6.2 | −3.3 | 6.1 | −1.7 |
| 6-Hour[†] | 5.0 | 5.7 | −14.0 | 5.6 | −12.0 |
| 9-Hour | 5.0 | 4.8 | 4.0 | 4.8 | 4.0 |
| 12-Hour[†] | 5.0 | 4.5 | 10.0 | 4.4 | 12.0 |
| 15-Hour | 5.0 | 4.0 | 20.0 | 4.2 | 16.0 |
| 18-Hour[†] | 5.0 | 4.3 | 14.0 | 4.0 | 20.0 |
| 21-Hour | 5.0 | 4.0 | 20.0 | 3.7 | 26.0 |
| 24-Hour[†] | 4.4 | 5.0 | −13.6 | 3.6 | 18.2 |
| 27-Hour | 4.5 | 4.6 | −2.2 | 3.7 | 17.8 |
| 30-Hour[†] | 4.1 | 4.0 | 2.4 | 3.6 | 12.2 |
| 33-Hour | 3.8 | 3.9 | −2.6 | 3.6 | 5.3 |
| 36-Hour[†] | 3.9 | 3.6 | 7.7 | 3.4 | 12.8 |
| 39-Hour | 3.4 | 3.1 | 8.8 | 3.8 | −11.8 |
| 42-Hour[†] | 3.5 | 3.3 | 5.7 | 3.2 | 8.6 |
| 45-Hour | 3.1 | 3.3 | −6.5 | 2.8 | 9.7 |
| 48-Hour[†] | 2.4 | 3.2 | −33.3 | 2.1 | 12.5 |
| AUC_1-24 Hour | 120.5 | 112.7 | 6.5 | 109.8 | 8.9 |
| AUC_6-24 Hour | 90.0 | 80.3 | 10.8 | 77.7 | 13.7 |
| AUC_12-24 Hour | 58.8 | 50.6 | 13.9 | 48.0 | 18.4 |

*Imputation method 1 is summarized.
[†]End of dose interval, assessment just prior to next scheduled dose.

In the ITT population, patients receiving the 800 mg ibuprofen dose experienced significantly less pain from study hour 9 through 24 when compared with morphine only (placebo) in addition to using less morphine. Patients receiving the 400 mg ibuprofen dose also experienced significantly less pain from study hour 9 through 24 (with the exception of the 12-hour time-point, p<0.10) when compared with morphine only (placebo). The VAS at rest AUC over 24 (p=0.003), from 6 through 24 (p<0.001) and from 12 through 24 (p<0.001) hours was lower in the patients receiving 800 mg ibuprofen compared to patients receiving morphine only (placebo). The VAS at rest AUC over 24 (p=0.095), from 6 through 24 (p=0.028) and from 12 through 24 (p=0.013) hours was lower in the patients receiving 400 mg ibuprofen compared to patients receiving morphine only (placebo). The percent pain reduction is presented below.

TABLE 4

Secondary Efficacy Variable, VAS Score measured at Rest,
Median Score and % Reduction vs Placebo, ITT*

| Study Hour | Placebo N = 134 (median) | 400 mg IVIb; N = 134 | | 800 mg IVIb; N = 138 | |
|---|---|---|---|---|---|
| | | (median) | % Reduction vs Placebo | (median) | % Reduction vs Placebo |
| 1-Hour | 7.0 | 7.0 | 0.0 | 7.0 | 0.0 |
| 2-Hour | 6.1 | 6.3 | −3.3 | 5.7 | 6.6 |
| 3-Hour | 5.0 | 5.1 | −2.0 | 5.0 | 0.0 |
| 6-Hour† | 4.0 | 4.3 | −7.5 | 4.0 | 0.0 |
| 9-Hour | 4.0 | 3.5 | 12.5 | 3.0 | 25.0 |
| 12-Hour† | 3.0 | 3.1 | −3.3 | 2.9 | 3.3 |
| 15-Hour | 3.3 | 2.6 | 21.2 | 2.6 | 21.2 |
| 18-Hour† | 3.0 | 2.9 | 3.3 | 2.0 | 33.3 |
| 21-Hour | 3.5 | 2.8 | 20.0 | 2.0 | 42.9 |
| 24-Hour† | 3.0 | 3.0 | 0.0 | 2.0 | 33.3 |
| 27-Hour | 3.0 | 3.1 | −3.3 | 2.2 | 26.7 |
| 30-Hour† | 2.7 | 2.4 | 11.1 | 2.3 | 14.8 |
| 33-Hour | 3.2 | 2.7 | 15.6 | 2.3 | 28.1 |
| 36-Hour† | 2.6 | 2.3 | 11.5 | 2.2 | 15.4 |
| 39-Hour | 1.8 | 2.1 | −16.7 | 2.7 | −50.0 |
| 42-Hour† | 2.0 | 2.1 | −5.0 | 1.9 | 5.0 |
| 45-Hour | 2.0 | 2.4 | −20.0 | 1.9 | 5.0 |
| 48-Hour† | 1.5 | 1.6 | −6.7 | 1.3 | 13.3 |
| AUC_1-24 Hour | 88.1 | 82.1 | 6.8 | 70.6 | 19.9 |
| AUC_6-24 Hour | 65.0 | 55.6 | 14.5 | 48.0 | 26.2 |
| AUC_12-24 Hour | 41.1 | 34.0 | 17.3 | 29.3 | 28.7 |

*Imputation method 1 is summarized.
†End of dose interval, assessment just prior to next scheduled dose.

In the EEP population, patients receiving the 800 mg ibuprofen dose experienced significantly less pain from study hour 9 through 24 when compared with morphine only (placebo) in addition to using less morphine. Patients receiving the 400 mg ibuprofen dose also experienced significantly less pain from study hour 9 through 24 (with the exception of the 12-hour time-point, p<0.10) when compared with morphine only (placebo). The VAS at rest AUC over 24 (p=0.095), from 6 through 24 (p=0.021) and from 12 through 24 (p=0.006) hours was lower in the patients receiving 800 mg ibuprofen compared to patients receiving morphine only (placebo). The VAS at rest AUC over 24 (p=0.408), from 6 through 24 (p=0.184) and from 12 through 24 (p=0.082) hours was lower in the patients receiving 400 mg ibuprofen compared to patients receiving morphine only (placebo). The percent pain reduction is presented below.

TABLE 5

Secondary Efficacy Variable, VAS Score measured at Rest,
Median Score and % Reduction vs Placebo, EEP*

| Study Hour | Placebo N = 115 (median) | 400 mg IVIb; N = 111 | | 800 mg IVIb; N = 116 | |
|---|---|---|---|---|---|
| | | (median) | % Reduction vs Placebo | (median) | % Reduction vs Placebo |
| 1-Hour | 7.0 | 7.0 | 0.0 | 7.0 | 0.0 |
| 2-Hour | 5.9 | 6.1 | −3.4 | 6.0 | −1.7 |
| 3-Hour | 5.0 | 5.0 | 0.0 | 5.0 | 0.0 |
| 6-Hour† | 4.0 | 4.0 | 0.0 | 5.0 | −25.0 |

TABLE 5-continued

Secondary Efficacy Variable, VAS Score measured at Rest,
Median Score and % Reduction vs Placebo, EEP*

|  | Placebo | 400 mg IVIb; N = 111 | | 800 mg IVIb; N = 116 | |
| --- | --- | --- | --- | --- | --- |
| Study Hour | N = 115 (median) | (median) | % Reduction vs Placebo | (median) | % Reduction vs Placebo |
| 9-Hour | 4.0 | 3.0 | 25.0 | 3.0 | 25.0 |
| 12-Hour† | 3.0 | 3.0 | 0.0 | 3.0 | 0.0 |
| 15-Hour | 3.0 | 2.0 | 33.3 | 2.8 | 6.7 |
| 18-Hour† | 3.0 | 2.9 | 3.3 | 2.0 | 33.3 |
| 21-Hour | 3.0 | 2.9 | 3.3 | 2.0 | 33.3 |
| 24-Hour† | 3.0 | 3.0 | 0.0 | 2.0 | 33.3 |
| 27-Hour | 3.1 | 3.0 | 3.2 | 2.3 | 25.8 |
| 30-Hour† | 2.8 | 2.5 | 10.7 | 2.4 | 14.3 |
| 33-Hour | 3.2 | 2.7 | 15.6 | 2.3 | 28.1 |
| 36-Hour† | 2.6 | 2.4 | 7.7 | 2.2 | 15.4 |
| 39-Hour | 1.8 | 2.1 | −16.7 | 2.7 | −50.0 |
| 42-Hour† | 2.0 | 2.1 | −5.0 | 1.8 | 10.0 |
| 45-Hour | 2.1 | 2.4 | −14.3 | 2.0 | 4.8 |
| 48-Hour† | 1.5 | 1.6 | −6.7 | 1.1 | 26.7 |
| AUC_1-24 Hour | 87.0 | 74.4 | 14.5 | 76.2 | 12.4 |
| AUC_6-24 Hour | 61.5 | 48.0 | 22.0 | 48.0 | 22.0 |
| AUC_12-24 Hour | 40.5 | 31.5 | 22.2 | 28.9 | 28.6 |

*Imputation method 1 is summarized.
†End of dose interval, assessment just prior to next scheduled dose.

A treatment failure was defined as a patient that required narcotic pain medication, other than morphine, or non-narcotic medications including the use of another NSAID through the treatment period. If other narcotics (other than morphine) or NSAIDS were started, ibuprofen/placebo was discontinued. In the ITT population, there was a numerical trend but not a statistically significant difference for fewer treatment failures in the ibuprofen groups compared to the placebo group: Placebo 10 (7%); 400 mg ibuprofen 7 (5%) p=0.452; 800 mg ibuprofen 4 (3%) p=0.089.

Time to GI motility was analyzed in the ITT and found to be statistically significant between the 400 mg ibuprofen treated group and placebo, but not found to be statistically significant between the 800 mg ibuprofen treated group and placebo: (in hours) Placebo (N=132) 24.6+1.78 SD; 400 mg ibuprofen (N=131) 20.1+1.28 SD, p=0.039; 800 mg ibuprofen (N=136) 21.6+1.50 SD, p=0.220. Time to GI motility was analyzed in the EEP and not found to be statistically significant between the 400 mg or 800 mg ibuprofen treated groups and placebo: (in hours) Placebo (N=115) 23.0+1.80 SD; 400 mg ibuprofen (N=110) 20.2+1.30 SD, p=0.189; 800 mg ibuprofen (N=116) 21.2+1.63 SD, p=0.389.

Time to ambulation was analyzed in the ITT population and found not to be statistically significant faster in the ibuprofen treated groups compared to the placebo group. Similarly, time to liquid intake and time to solid intake was analyzed in the ITT and not found to be statistically significant between the ibuprofen treated group and placebo. Length of hospital stay was analyzed in the ITT and not found to be statistically significant between treated and placebo groups.

In a combined safety assessment, the occurrence of diffuse pruritus, overt respiratory depression, need for post-operative urinary indwelling catheter, incidence of post-operative vomiting or need for anti-emetic medication, Richmond Agitation Sedation Scale <−3 was recorded as a value of one and the mean score was compared between groups. The combined safety assessment score was analyzed in the ITT and found to be statistically significant between the 400 mg ibuprofen treated group and placebo, but not the 800 mg ibuprofen mg treated group: Placebo (N=134) 1.0+0.71 SD; 400 mg ibuprofen (N=133) 0.8+0.63 SD, p=0.011; 800 mg ibuprofen (N=137) 0.9+0.78 SD, p=0.154. The combined safety assessment score was analyzed in the EEP and not found to be statistically significant between active and placebo groups: Placebo (N=115) 0.9+0.67 SD; 400 mg ibuprofen (N=111) 0.8+0.62 SD, p=0.119; 800 mg ibuprofen (N=116) 0.9+0.76 SD, p=0.520.

Conclusions

With respect to efficacy, in the 24 hours after surgery, 800 mg intravenous ibuprofen reduced opioid use, and resulted in less pain at rest and with movement by patient self assessment compared to placebo, while 400 mg intravenous ibuprofen resulted in less pain at rest and with movement but not in reduced opioid use.

Specifically, compared to placebo there was a reduction in the use of morphine through 24 hours in patients receiving 800 mg ibuprofen (p=0.030), but not in patients receiving 400 mg ibuprofen (p=0.458). In the 342 efficacy evaluable patients, there was a 25.6% reduction in median morphine consumption in patients receiving 800 mg ibuprofen and a 4.4% reduction in median morphine consumption in patients receiving 400 mg ibuprofen. In the 161 patients who underwent an abdominal hysterectomy, there was a 41.1% reduction in median morphine consumption in patients receiving 800 mg ibuprofen and a 15.9% reduction in median morphine consumption in patients receiving 400 mg ibuprofen. In addition to the morphine sparing-effect, patients receiving both 400 mg and 800 mg ibuprofen experienced a significant reduction in pain as measured by the VAS with movement and at rest area under the curve for the first 24 hours, from 6 through 24 hours, and from 12 through 24 hours after surgery and a reduction in pain as measured by the VAS at rest area under the curve for the first 24 hours (p=0.003), from 6 through 24 hours (p<0.001), and from 12 through 24 hours (p<0.001). Patients receiving 400 mg ibuprofen experienced a reduction in pain as measured by the VAS with movement area under the curve for the first 24 hours (p=0.033), from 6 through 24 hours (p=0.008), and from 12 through 24 hours (p=0.006) after surgery and a reduction in pain as measured by the VAS at rest area under the curve for the first 24 hours (p=0.095), from 6 through 24 hours (p=0.0281), and from 12 through 24 hours (p=0.013).

There was a numerical but not a statistically significant difference for fewer treatment failures in the ibuprofen groups compared to the placebo group: Placebo 10 (7%); 400 mg ibuprofen 7 (5%) p=0.452; 800 mg ibuprofen 4 (3%) p=0.089 (p values vs. placebo). Thus, there were nominally fewer treatment failures in the ibuprofen group.

No safety concerns were identified as there were no significant differences in the number of patients experiencing serious adverse events between groups. Further, there were no differences between treatment groups with respect to adverse events and clinical laboratory assessments commonly associated with oral ibuprofen use. Compared to placebo, treatment with intravenous ibuprofen did not result in more adverse events, serious adverse events, or abnormalities of safety lab measurements. Specifically, there were no additional bleeding or renal complications resulting from ibuprofen use. There was a significant reduction in the number of patients experiencing gastrointestinal disorders and fever in both the 400 mg IVIb and 800 mg IVIb treated participants when compared to morphine only (placebo) treated participants. There was a significant reduction in the number of patients experiencing nausea in the 400 mg IVIb and trending toward significance in the 800 mg IVIb treated participants. There was a significant reduction in patients experiencing diarrhea in the 800 mg IVIb treated group compared to the morphine only (placebo) group. Dizziness was experienced more often in the 800 mg IVIb treated participants when compared to placebo treated participants. There were no patient deaths during the 14 day study.

Intravenous ibuprofen is an effective analgesic that is safe and well tolerated when administered as an 800 mg dose every six hours in post-operative patients.

Example 2

Example 2 was a randomized, double-blind, placebo controlled study to evaluate treatment of pain in post-operative adult patients. The primary objective of this study was to determine the efficacy of intravenous ibuprofen compared to placebo for the treatment of post-operative pain as measured by reduction in the requirement for the narcotic analgesic, morphine, post surgery. Secondary objectives were 1) to determine the efficacy of IVIb compared to placebo for the treatment of post-operative pain as determined by the patient's self assessment of pain; 2) to determine the safety of IVIb compared to placebo for the treatment of post-operative pain; 3) to determine whether the use of IVIb reduces the incidence of opioid related side-effects to determine the optimal dose of ibuprofen for post-operative pain treatment.

To be eligible for this study, the patients met the following inclusion criteria: 1) scheduled for elective abdominal hysterectomy surgery with anticipated need for post-operative I.V. morphine analgesia with anticipated use of greater than 24 hours; 2) adequate IV access; and 3) anticipated hospital stay greater than 24 hours. The study exclusion criteria required patients only between the ages of 18 and 70 years old. The 800 mg IVIb ibuprofen dose was selected for use based on the outcome of the study of Example 1. Efficacy was measured by comparing the reduction in morphine use over the 24 hours immediately post surgery. Efficacy was measured by reduction in the requirement for the narcotic analgesic, morphine, in the 24 hours post surgery.

A total of 185 participants were randomized into one of two groups, with participants receiving either: 1) Placebo (normal saline, 100 ml, intravenous saline) or (2) 800 mg ibuprofen infused over 30 minutes intravenously every 6 hours. The Clinical Trial Material ("CTM") was mixed in 250 mL normal saline. Saline was chosen as the control group (placebo) for this study, to ensure blinding and allow for analysis of treatment effect.

By protocol, patients were to be dosed every six hours for five doses, then as necessary (PRN) for pain every six hours for up to five days post surgery. However, after 24 hours through day 5, CTM had to be discontinued if there was a requirement for narcotic pain medication other than morphine or non-narcotic medications including the use of another NSAID. Further, after 24 hours through day 5, CTM may have been discontinued if there was resolution of pain, no IV access or discharge from the hospital. The number of doses administered ranged from 1-13 with a median of five doses across treatment groups and mean by treatment group of: 800 mg intravenous ibuprofen 6 (+SD 2.2); Placebo 5 (+SD 1.5).

All 185 patients had CTM discontinued, prior to treatment day 5. The primary reason for discontinuation was due to intravenous access being discontinued: intravenous ibuprofen 48 (48%); Placebo 37 (43%). Groups were stratified according to two age groups: <45 and >45 to 80 years of age and two weight groups: <75 kg and >75 kg of weight.

The study participants were randomized based on criteria for an efficacy evaluable population (EEP) versus an intent to treat population (ITT). The ITT included all patients who were randomized and received at least a partial dose of ibuprofen. The intent-to-treat population (ITT) consists of AT patients who received at least one post-surgical dose of CTM or at least one dose of morphine for break-through pain. The efficacy evaluable population (EEP) consists of all ITT patients who received each of the first five doses of CTM within 60 minutes of the scheduled time and who have the 6-hour and 28-hour VAS with movement assessments.

Eligible patients were randomized to one of the two treatment groups. All patients were able (but were not required) to receive morphine until approximately 45 minutes before the end of the surgical procedure. After that time, only fentanyl was allowed until the end of the operation. The first dose of ibuprofen was administered at approximately the initiation of skin closure. Upon discharge from the operating room, patients had access to morphine (approximately 1-2 mg q 5 minutes) upon patient request or delivered by patient-controlled analgesia (PCA). Seven subsequent doses of ibuprofen were administered intravenously over 30 minutes every 6 hours over the next two days under the protocol, for a total of 8 doses. Dosing was discontinued after 24 hours (4 doses) for certain patients due to 1) ability to tolerate oral pain medication; 2) resolution of pain; 3) no IV access; or 4) discharge from the hospital. For patients that received 8 scheduled doses of ibuprofen, additional ibuprofen could be administered as needed for pain every 6 hours through 5 days post surgery. Other than ibuprofen or placebo, only morphine was administered for pain. Upon discharge from the operating room, patients had access to 1 mg morphine every 5 minutes upon request or by patient-controlled analgesia (PCA). If adequate pain control was not achieved the dose of morphine could have been increased to 2 mg morphine every 5 minutes. Additional morphine could be administered at the discretion of the treating physician if adequate pain control had still not been achieved. Patients given non-morphine analgesics were classified as treatment failures. Treatment failures were not replaced.

Patients were evaluated and compared for morphine requirements between the active doses and placebo using analysis of variance and covariance procedures at an overall alpha level of 0.05. Secondary efficacy parameters were also evaluated and compared among the treatment groups using appropriate statistical methods described in the statistical analysis section of the protocol. Safety information was compared between the treatment groups using Chi-Square or Cochran-Mantel-Haenszel test. Demographic, background and baseline information among the treatment groups was also described.

Analysis of the primary efficacy parameters were conducted both on the ITT and EEP populations.

The primary endpoint for the study was reduction in the requirement for morphine use in the 24 hours following surgery as measured by total morphine usage compared to placebo. Analysis of variance and covariance procedures were used to compare the reduction in the requirement for morphine use in the 24 hours following surgery among the treatment groups. Dunnet's test was used as a multiple comparison test to compare active dose groups with the placebo group at an overall alpha level of 0.05. In the primary model, center was introduced as a covariate. Center-by-Treatment interaction was examined to evaluate the consistency of results among centers for the primary efficacy endpoint, morphine requirements post-surgery. Type of surgery, weight, gender and other covariates identified through the demographic, background and baseline analysis were introduced as secondary covariates for sensitivity analysis and robustness.

Morphine use since the last assessment was obtained every three hours through the 48 hour treatment period.

The secondary endpoints were to include reduced pain intensity as measured by the patient's self-assessment of pain intensity as reported by a visual analog scale (VAS) of 0-10, with 0 being no pain and 10 being intense pain, time to first subsequent narcotic analgesia for breakthrough pain and nocturnal awakenings due to pain.

To evaluate the secondary objective of determining whether the addition of IVIb reduces the incidence of opioid related side-effects, the following endpoints were measured: (a) GI motility as assessed by return of bowel sounds, flatulence, or bowel movement (b) Combined Safety Assessment (occurrence of any of the following during the 48 hour treatment period received a rating of one: diffuse pruritus, overt respiratory depression requiring treatment; the combined total and individual incidences were evaluated), need for post-operative urinary indwelling catheter (after initial removal of surgical catheter), incidence of post-operative vomiting or need for anti-emetic medication, Richmond Agitation Sedation Scale (<−3), (c) Resumption of ambulation, (d) Resumption of liquid intake and solid diet, and (e) Length of hospital stay.

In the ITT, patients used a mean of 47.3 mg morphine and a median 43.5 mg morphine in the Ibuprofen group and a mean of 55.9 mg and a median of 54.0 mg morphine in the placebo group. In the EEP, patients used a mean of 45.5 mg morphine and a median 42.0 mg morphine in the Ibuprofen group and a mean of 54.3 mg and a median of 53.5 mg morphine in the placebo group. There was a difference between treatment groups in both the ITT and EEP with respect to morphine consumption (ITT Ibuprofen vs. placebo, $p<0.001$; EEP Ibuprofen vs. placebo, $p<0.001$). Summary statistics are presented below in Table 6.

Per the pre-defined analyses in the statistical analysis plan (SAP), statistical testing was performed on the transformed morphine requirement.

TABLE 6

Summary Reduction in Morphine Use by Treatment Group

| | Intent-to-Treat | | Efficacy Evaluable | |
| --- | --- | --- | --- | --- |
| | Placebo (n = 153) | Ibuprofen (n = 166) | Placebo (n = 137) | Ibuprofen (n = 150) |
| Morphine Requirement (mg) | | | | |
| Mean (SD) | 55.9 (20.6) | 47.3 (25.6) | 54.3 (20.5) | 45.5 (24.6) |
| Median | 54.0 | 43.5 | 53.5 | 42.0 |
| Min, Max | 14.5, 114.0 | 4.0, 143.3 | 14.5, 114.0 | 4.0, 143.3 |
| Transformed Morphine Requirement (mg) | | | | |
| Mean (SD) | 13.4 (3.1) | 11.8 (4.0) | 12.1 (2.7) | 10.7 (3.5) |
| LSMeans (SE)[1] | 13.6 (0.4) | 12.1 (0.4) | 12.2 (0.4) | 10.8 (0.3) |
| Median | 13.4 | 11.8 | 12.3 | 10.7 |
| Min, Max | 5.8, 20.6 | 2.0, 23.5 | 5.5, 18.7 | 2.0, 21.2 |
| Pairwise Comparison to Placebo | | | | |
| p-value[2] | | <0.001 | | <0.001 |

[1]Data are transformed using the Box Cox transformation. LS means are adjusted for age group, weight group, randomization center, and treatment group.
[2]The analysis is based on a linear 4-way ANOVA model with fixed effects for age group, weight group, randomization center, and treatment group.

Table 7 shows the median reduction in morphine use in the 24 hours following surgery in the Ibuprofen group compared to the control group.

TABLE 7

Primary Efficacy Variable: Median Morphine Usage in the 24 Hours Following Surgery

| | | Placebo | Ibuprofen | % Reduction |
| --- | --- | --- | --- | --- |
| ITT | N | 153 | 166 | |
| | Median | 54.0 | 43.5 | 19.5% |
| EEP | N | 137 | 150 | |
| | Median | 53.5 | 42.0 | 21.5% |

Pain was measured at rest and with movement by patient's self-assessment using a Visual Analog Scale (VAS) from 0-10 with 0 being no pain and 10 being intense pain. VAS assessments were performed at hours 1, 3, 6, 9, 12, 15, 18, 24, 27, 30, 33, 36, 39, 42, 45, 48 and daily through day 5. Because the protocol did not require patients to be awakened to obtain pain assessments, missing pain assessments were anticipated.

To account for the missing pain assessments, two methods were used to impute values. To determine the difference in overall pain at differing time-points, the area under the VAS pain curve during the first 24 hours, between 6 and 24 hours and between 12 and 24 hours were analyzed.

In the ITT population, patients receiving Ibuprofen experienced less pain from study hour 15-24 while using approximately 20% less morphine when compared with morphine only (placebo) patients. The VAS with movement AUC over 24 (p=0.009), from 6 through 24 (p<0.001), and from 12 through 24 (p<0.001) hours was lower in the Ibuprofen patients compared to the morphine only (placebo) patients. The percent pain reduction is presented below.

TABLE 8

Secondary Efficacy Variable, VAS Score measured with Movement, Median Score and % Reduction vs Placebo, ITT*

| Study Hour | Placebo n = 153 (median) | Ibuprofen n = 166 (median) | % Reduction vs Placebo |
|---|---|---|---|
| 1-Hour | 8.0 | 9.0 | −12.5 |
| 3-Hour | 7.0 | 7.0 | 0.0 |
| 6-Hour† | 6.0 | 6.0 | 0.0 |
| 9-Hour | 5.2 | 5.0 | 3.8 |
| 12-Hour† | 4.8 | 4.3 | 10.4 |
| 15-Hour | 4.4 | 3.4 | 22.7 |
| 18-Hour† | 4.3 | 3.0 | 30.2 |
| 21-Hour | 4.6 | 3.0 | 34.8 |
| 24-Hour† | 4.5 | 3.6 | 20.0 |
| AUC_1-24 Hour | 121.0 | 103.5 | 14.5 |
| AUC_6-24 Hour | 85.4 | 68.3 | 20.0 |
| AUC_12-24 Hour | 53.8 | 41.0 | 23.8 |

*Imputation method 1 is summarized.
†End of dose interval, assessment just prior to next scheduled dose.

In the EEP population, in addition to the morphine sparing effect, there were statistically significant reductions in pain assessment scores in the 800 mg group from study hour 15-24 compared with morphine only (placebo). The percent pain reduction at individual time-points is presented. The VAS with movement AUC over 24 (p=0.021), from 6 through 24 (p=0.004), and from 12 through 24 (p<0.001) hours was lower in the Ibuprofen patients compared to the morphine only (placebo) patients. The percent pain reduction is presented below.

TABLE 9

Secondary Efficacy Variable, VAS Score measured with Movement, Median Score and % Reduction vs Placebo, EEP*

| Study Hour | Placebo n = 153 (median) | Ibuprofen n = 166 (median) | % Reduction vs Placebo |
|---|---|---|---|
| 1-Hour | 8.0 | 9.0 | −12.5 |
| 3-Hour | 7.0 | 7.0 | 0.0 |
| 6-Hour† | 6.0 | 6.0 | 0.0 |
| 9-Hour | 5.0 | 5.0 | 0.0 |
| 12-Hour† | 5.0 | 4.0 | 20.0 |
| 15-Hour | 4.4 | 3.0 | 31.8 |
| 18-Hour† | 4.0 | 3.0 | 25.0 |
| 21-Hour | 4.0 | 3.0 | 25.0 |
| 24-Hour† | 5.0 | 3.0 | 40.0 |
| AUC_1-24 Hour | 121.0 | 95.8 | 20.8 |
| AUC_6-24 Hour | 88.0 | 66.0 | 25.0 |
| AUC_12-24 Hour | 54.0 | 39.0 | 27.8 |

*Imputation method 1 is summarized.
†End of dose interval, assessment just prior to next scheduled dose.

In the ITT population, in addition to the morphine sparing effect, patients in the Ibuprofen group had statistically significantly less pain from study hour 9-24 when compared with morphine only (placebo) patients. The percent pain reduction at individual time-points is presented. The VAS at Rest AUC over 24 (p=0.003), from 6 through 24 (p<0.001), and from 12 through 24 (p<0.001) hours was lower in the Ibuprofen patients compared to the morphine only (placebo) patients. The percent pain reduction is presented below.

TABLE 10

Secondary Efficacy Variable, VAS Score measured at Rest, Median Score and % Reduction vs Placebo, ITT*

| Study Hour | Placebo n = 153 (median) | Ibuprofen n = 166 (median) | % Reduction vs Placebo |
|---|---|---|---|
| 1-Hour | 8.0 | 8.0 | 0.0 |
| 3-Hour | 6.0 | 5.7 | 5.0 |
| 6-Hour† | 4.5 | 4.0 | 11.1 |
| 9-Hour | 4.0 | 3.0 | 25.0 |
| 12-Hour† | 3.4 | 2.7 | 20.6 |
| 15-Hour | 2.9 | 2.0 | 31.0 |
| 18-Hour† | 2.9 | 2.0 | 31.0 |
| 21-Hour | 3.0 | 2.0 | 33.3 |
| 24-Hour† | 2.9 | 2.0 | 31.0 |
| AUC_1-24 Hour | 88.5 | 70.1 | 20.8 |
| AUC_6-24 Hour | 59.3 | 43.0 | 27.5 |
| AUC_12-24 Hour | 36.0 | 22.5 | 37.5 |

*Imputation method 1 is summarized.
†End of dose interval, assessment just prior to next scheduled dose.

In the EEP population, there were statistically significant reductions in pain in the Ibuprofen group compared to the morphine only (placebo) group from study hour 9-24 (with the exception of hour 12). The VAS at Rest AUC over 24 (p=0.009), from 6 through 24 (p<0.001), and from 12 through 24 (p<0.001) hours was lower in the Ibuprofen patients compared to the morphine only (placebo) patients. The percent pain reduction is presented below.

TABLE 11

Secondary Efficacy Variable, VAS Score measured at Rest, Median Score and % Reduction vs Placebo, EEP*

| Study Hour | Placebo n = 153 (median) | Ibuprofen n = 166 (median) | % Reduction vs Placebo |
|---|---|---|---|
| 1-Hour | 8.0 | 8.0 | 0.0 |
| 3-Hour | 6.0 | 5.0 | 16.7 |
| 6-Hour† | 5.0 | 4.0 | 20.0 |
| 9-Hour | 4.0 | 3.0 | 25.0 |
| 12-Hour† | 3.0 | 2.5 | 16.7 |
| 15-Hour | 3.0 | 2.0 | 33.3 |
| 18-Hour† | 3.0 | 2.0 | 33.3 |
| 21-Hour | 3.0 | 1.0 | 66.7 |
| 24-Hour† | 3.0 | 2.0 | 33.3 |
| AUC_1-24 Hour | 88.0 | 67.3 | 23.5 |
| AUC_6-24 Hour | 58.5 | 40.5 | 30.8 |
| AUC_12-24 Hour | 36.0 | 21.0 | 41.7 |

*Imputation method 1 is summarized.
†End of dose interval, assessment just prior to next scheduled dose.

A treatment failure was defined as a patient that required narcotic pain medication, other than morphine, or non-narcotic medications including the use of another NSAID through the treatment period. If other narcotics (other than morphine) or NSAIDS were started, CTM was discontinued. In the ITT population, there was a numerical but not a statistically significant difference for fewer treatment failures in the Ibuprofen group compared to the morphine only (placebo) group: Ibuprofen 7 (4%); Placebo 11 (7%) p=0.250.

Time (hours) to GI motility in the ITT was similar between groups: Ibuprofen (N=166) 9.4+0.87 SD; Placebo (N=153) 11.2+1.40 SD, p=0.512. Similarly, time (hours) to GI motility in the EEP was not different between groups: Ibuprofen (N=150) 9.2+0.90 SD; Placebo (N=137) 11.1+1.49 SD, p=0.520.

Time to ambulation (hours) in the ITT population was faster in the Ibuprofen treated group (N=166) 23.4+0.50 compared to the morphine only (placebo) group (N=153) 25.3+0.94, p=0.009. Similarly, time to ambulation in the EEP population was faster in the Ibuprofen treated group (N=150) 23.5+0.53 compared to placebo (N=137) 25.6+1.01, p=0.018.

Time to liquid intake in the ITT cohort did not differ between Ibuprofen (N=166) 12.1+0.83 and placebo groups (N=153) 13.4+0.75, p=0.520. Likewise, time to liquid intake in the EEP cohort did not differ between Ibuprofen (N=150) 12.4+0.89; and placebo groups (N=137) 13.0+0.77, p=0.923.

Time to solid diet (in hours) in the ITT cohort did not differ between Ibuprofen (N=166) 41.0+2.46; and placebo groups (N=153) 41.1+1.75, p=0.397. Similarly time to solid diet in the EEP cohort did not differ between Ibuprofen (N=150) 39.1+1.42; and placebo groups (N=137) 41.9+1.88, p=0.161.

Length of hospital stay in the ITT cohort was not statistically different between Ibuprofen (N=166) 62.4+21.01; and placebo groups (N=153) 64.9+19.57, p=0.142. Similarly, length of hospital stay in the EEP did not differ between Ibuprofen (N=150) 62.8+21.58; and placebo groups (N=137) 65.7+19.73, p=0.088.

In a combined safety assessment, the occurrence of diffuse pruritus, overt respiratory depression, need for post-operative urinary indwelling catheter, incidence of post-operative vomiting or need for anti-emetic medication, Richmond Agitation Sedation Scale <−3 was recorded as a value of one and the mean score was compared between groups. The combined safety assessment score was analyzed in the ITT and not found to be statistically different between the Ibuprofen treated group and placebo: 800 mg Ibuprofen (N=166) 0.7+0.71; Placebo (N=153) 0.8+0.73, p=0.228. The combined safety assessment score was analyzed in the EEP and not found to be statistically different between active and placebo groups: Ibuprofen (N=150) 0.7+0.70; Placebo (N=137) 0.8+0.73, p=0.174.

The imputed values of the 24-hour morphine usage were analyzed with SAS® PROC GLM, Version 9.1.3. Factors for treatment, age group, weight group and center were included in the model. The following approach (as predefined by the statistical analysis plan and presented in Table 19 below) was employed in evaluating the efficacy variables. The residuals of the simplest model (Linear) were assessed for normality. Because the residuals violate model assumptions for normality (as demonstrated by the Kolmogorov-Smirnov test presented below), additional techniques were applied to investigate the robustness of conclusions. Among the methods that were utilized are log and Box-Cox transformations, followed then by non-parametric testing. The rank transformation was applied to confirm the results.

Table 27 summarizes the analysis of the primary endpoint, the total morphine used (mg) in the first 24 hours following surgery. There are 2 imputation methods, 2 study populations and 4 transformations of the primary endpoint presented below. The conclusions from the two imputations methods were the same as were the results from the two study populations, ITT and EEP.

Conclusions

In the 24 hours after surgery, intravenous ibuprofen reduced opioid use, and resulted in less pain at rest and with movement by patient self assessment compared to placebo.

IV Ibuprofen treated patients used significantly less morphine (p<0.001) compared to placebo patients. The IV ibuprofen treated efficacy evaluable patients had a 21% reduction in median morphine consumption compared to placebo patients. In addition to the morphine sparing-effect, patients receiving 800 mg IV ibuprofen experienced a significant reduction in pain, ranging from 15 to 42%, as measured by the VAS with movement and at rest area under the curve for the first 24 hours, from 6 through 24 hours, and from 12 through 24 hours after surgery. Time to ambulation was significantly faster in the Ibuprofen treated group and there were nominally fewer treatment failures in the Ibuprofen group.

No safety concerns were identified as there were no significant differences in the number of patients experiencing adverse events or serious adverse events between groups. Further, there were no differences between treatment groups with respect to adverse events and clinical laboratory assessments commonly associated with oral ibuprofen use.

Intravenous ibuprofen is an effective analgesic that is safe and well tolerated when administered as an 800 mg dose every six hours in post-operative patient and is safe and effective for reducing opioid use.

Example 3

Example 3 was a randomized, double-blind, placebo controlled study to evaluate the efficacy and safety of intravenous ibuprofen for the management of pain in patients undergoing orthopedic surgical procedures through the measurement of visual and verbal pain assessments and its potential morphine-sparing effect. The primary objective of this study was to determine the efficacy of intravenous ibuprofen compared to placebo for the treatment of post-operative pain demonstrated by patients self assessment of pain with movement using a visual analog scale (VAS). The secondary objectives of this study were: 1) to determine the efficacy of intravenous ibuprofen compared to placebo for the treatment of post-operative pain demonstrated by patients self assessment of pain at rest using a VAS; 2) to determine the efficacy of intravenous ibuprofen compared to placebo for the treatment of post-operative pain demonstrated by patients self assessment of pain at rest using a verbal response scale (VRS); 3) to determine the efficacy of intravenous ibuprofen compared to placebo for the treatment of post-operative pain demonstrated by patients self assessment of pain with movement using a VRS; 4) to determine the efficacy of intravenous ibuprofen compared to placebo for the treatment of post-operative pain demonstrated by reduction in the requirement for the narcotic analgesic, morphine, post surgery; 5) to determine the efficacy of intravenous ibuprofen compared to placebo for the treatment of post-operative pain demonstrated by time to first request for the narcotic analgesic, morphine, post surgery; 6) to determine the safety of intravenous ibuprofen compared to placebo for the treatment post-operative pain; 7) to determine whether the use of intravenous ibuprofen reduces the incidence of opioid related side effects.

To be eligible for this study, the patients met the following inclusion criteria: 1) scheduled for elective hip or knee replacement, reconstruction or arthroplasty surgery with anticipated need for post-operative I.V. morphine analgesia with anticipated use of >28 hours: 2) adequate IV access; 3) anticipated hospital stay greater than 24 hours. The study exclusion criteria required patients only between the ages of 18 and 80 years old. The 800 mg IVIb ibuprofen dose was selected for use based on the outcome of Example 1. Efficacy was measured by comparing the reduction in morphine use over the 24 hours immediately post surgery. Efficacy was measured by reduction in the requirement for the narcotic analgesic, morphine, in the 24 hours post surgery.

A total of 185 participants were randomized into one of two groups, with participants receiving either: 1) Placebo (normal saline, 100 ml, intravenous saline) or (2) 800 mg ibuprofen infused over 30 minutes intravenously every 6 hours. The Clinical Trial Material ("CTM") was mixed in 250 mL normal saline. Saline was chosen as the control group (placebo) for this study, to ensure blinding and allow for analysis of treatment effect. The duration of treatment was up to 5 days post surgery. The dosing was one dose every 6 hours for 8 doses, then as needed for pain every 6 hours for up to 5 days post surgery.

In this study, the first dose of CTM was administered prior to the surgical procedure to determine if a reduction of pain would be seen as quickly as the first pain measurement post-surgery. The participants were randomized in this study as enrollment was based on criteria for an efficacy evaluable population (EEP) versus an intent to treat population (ITT). Groups were stratified according to two age groups: <45 and >45 to 70 years of age and two weight groups: <75 kg and >75 kg of weight.

The study participants were randomized based on criteria for an efficacy evaluable population (EEP) versus an intent to treat population (ITT). The ITT included all patients who were randomized and received at least a partial dose of ibuprofen. Patients included in the ITT who had no major protocol violations with regard to inclusion or exclusion criteria or study conduct and had all primary efficacy assessments were eligible for inclusion in the EEP: specifically, these were patients included in the ITT who received at least the first four doses of ibuprofen administered within +60 minutes of the scheduled administration time.

Eligible patients were randomized to one of the two treatment groups. The study duration was seven days. First dose of CTM was administered at approximately the initiation of anesthesia, prior to the surgical procedure. Per protocol, four subsequent doses of CTM were to be administered every six hours over the next 24 hours. If the patient received five scheduled doses of CTM, additional CTM could be administered as needed every six hours through the 120-hour Treatment Period. Other than ibuprofen or placebo, only morphine was administered for pain.

Patients were evaluated and compared for morphine requirements between the active doses and placebo using analysis of variance and covariance procedures at an overall alpha level of 0.05. Secondary efficacy parameters were also evaluated and compared among the treatment groups using appropriate statistical methods described in the statistical analysis section of the protocol. For the adverse events, instead of using an unadjusted Chi-square test and a Cochran-Mantel-Haenszel test adjusted for center to compare treatment groups with respect to the numbers of patients reporting AEs, a Fisher's exact test was used to compare treatment groups for any AE that was reported by five or more patients.

To evaluate the primary objective of efficacy of the intravenous ibuprofen compared to placebo for the treatment of post-operative pain demonstrated by patients self assessment of pain using a visual analog scale, the following endpoint was measured: The AUC-VAS (active treatment) assessed with movement during the post-operative period (study hour-6 through hour-28), as compared to placebo treatment.

To evaluate the secondary objective of determining the efficacy of intravenous ibuprofen compared to placebo for the treatment of post-operative pain, the following endpoints were measured: Reduction in the post-operative morphine use from post-surgery through study hour 28 measured by total morphine usage compared to placebo; the AUC-VAS (active treatment) assessed at rest during the post-operative period (study hour-6 through hour-28), as compared to placebo treatment; the AUC-VAS (active treatment) assessed at rest during the post-operative period through treatment, as compared to placebo treatment; the AUC-VAS (active treatment) assessed with movement during the post-operative period through treatment, as compared to placebo treatment; the AUC-VRS (active treatment) assessed during the post-operative period (study hour-6 through hour-28), as compared to placebo treatment; the AUC-VRS (active treatment) assessed with movement during the post-operative period through treatment, as compared to placebo treatment; reduced pain intensity at rest or with movement as measured by the patient's self-assessment of pain intensity as reported by VAS assessed initially post-surgery; and reduction in the post-operative morphine use from post-surgery through study hour 28 measured by total morphine usage compared to placebo.

To evaluate the secondary objective of determining whether the addition of intravenous ibuprofen reduces the incidence of opioid related side-effects, the following individual endpoints were measured: time to GI motility as measured by return of bowel sounds, flatulence, or bowel activity; diffuse pruritis; overt respiratory depression; need for post-operative urinary indwelling catheter (after initial removal of surgical catheter); incidence of post-operative vomiting or need for anti-emetic medication; Richmond Agitation Sedation Scale (RASS); resumption of ambulation; resumption of liquid intake and solid diet; and length of hospital stay.

To evaluate the secondary objective of determining whether the addition of intravenous ibuprofen reduces the incidence of opioid related side-effects, the following composite assessment was evaluated: Combined Safety Assessment: Occurrence of each of the following during the treatment period would receive a rating of one: (a) diffuse pruritis, (b) overt respiratory depression, (c) need for post-operative urinary indwelling catheter (after initial removal of surgical catheter), (d) incidence of post-operative vomiting or need for anti-emetic medication, (e) Richmond Agitation Sedation Scale ($<-3$). The mean total number of occurrences of all events (total from 0-5) for each patient was compared among treatment groups.

Efficacy of intravenous ibuprofen to treat post-operative pain was demonstrated by measuring the patient's self assessment of pain with movement using a visual analog scale during the post-operative period (study hour-6 through hour-28). VAS assessments were performed immediately following surgery and at hours 6, 8, 12, 16, 20, 24 and 28 (for the primary endpoint).

Patients receiving 800 mg intravenous ibuprofen experienced less pain, demonstrated by patients' self assessment of pain using a visual analog scale, the AUC-VAS assessed with movement. Table 12 indicates that patients in the all treated population experienced a 25.8% decrease in the mean AUC-VAS in the post-operative period.

TABLE 12

Summary of Pain with Movement Measured with VAS, AT

| 6-28 hours | AUC (AT) | |
| --- | --- | --- |
| (post-operative period) | Placebo (N = 86) | 800 mg (N = 99) |
| Mean (SD) | 1307.8 (388.7) | 970.1 (422.2) |
| LS Means (SE) | 1326.1 (82.0) | 1005.0 (81.5) |
| Median | 1304.6 | 946.2 |
| LS Means Difference (95% CI) | | −321.1 (−436.7, −205.4) |
| p-value vs Placebo[1] | | <0.001 |

[1]The analysis is based on a linear ANCOVA model with fixed effects for age group, weight group, randomization center, and treatment group. The p-values and 95% confidence intervals are based on the difference in the LS Means from the final ANCOVA model.

Table 13 shows that patients in the ITT population experienced a 25.8% decrease in the mean AUC-VAS in the post-operative period.

TABLE 13

Summary of Pain with Movement Measured with VAS, ITT

| 6-28 hours | AUC (ITT) | |
| --- | --- | --- |
| (post-operative period) | Placebo (N = 84) | 800 mg (N = 95) |
| Mean (SD) | 1307.8 (393.3) | 970.2 (431.0) |
| LS Means (SE) | 1327.6 (85.6) | 1006.7 (83.9) |
| Median | 1304.6 | 932.7 |
| LS Means Difference (95% CI) | | −320.9 (−440.7, −201.1) |
| p-value vs Placebo[1] | | <0.001 |

[1]The analysis is based on a linear ANCOVA model with fixed effects for age group, weight group, randomization center, and treatment group. The p-values and 95% confidence intervals are based on the difference in the LS Means from the final ANCOVA model.

Table 14 shows that patients in the EEP experienced a 22.7% decrease in the mean AUC-VAS in the post-operative period.

TABLE 14

Summary of Pain with Movement Measured with VAS, EEP

| 6-28 hours | AUC (EEP) | |
| --- | --- | --- |
| (post-operative period) | Placebo (N = 64) | 800 mg (N = 77) |
| Mean (SD) | 1254.9 (403.6) | 970.3 (440.2) |
| LS Means (SE) | 1309.0 (97.3) | 1029.7 (91.7) |
| Median | 1290.4 | 900.5 |
| LS Means Difference (95% CI) | | −279.3 (−420.7, −138.0) |
| p-value vs Placebo[1] | | <0.001 |

[1]The analysis is based on a linear ANCOVA model with fixed effects for age group, weight group, randomization center, and treatment group. The p-values and 95% confidence intervals are based on the difference in the LS Means from the final ANCOVA model.

Secondary Endpoint: Morphine Use

Efficacy of intravenous ibuprofen to treat post-operative pain was demonstrated by measuring the reduction in the morphine use from post-surgery through study hour 28, compared to placebo.

Patients receiving 800 mg intravenous ibuprofen used less morphine compared to those receiving placebo. Table 15 indicates that patients in the AT population experienced a 30.9% decrease in the mean morphine used in the postoperative period.

TABLE 15

Summary of Reduction in Morphine Use, AT

| | Morphine Requirement | |
| --- | --- | --- |
| Post-Op-28 hours | Placebo (N = 86) | 800 mg (N = 99) |
| N | 85 | 97 |
| Mean (SD) | 59.5 (29.9) | 41.1 (27.3) |
| LS Means (SE) | 60.9 (5.7) | 44.3 (5.7) |
| Median | 58.0 | 38.0 |
| LS Means Difference (95% CI) | | −16.6 (−24.7, −8.4) |
| p-value vs Placebo[1] | | <0.001 |

[1]The analysis is based on a linear ANCOVA model with fixed effects for age group, weight group, randomization center, and treatment group. The p-values and 95% confidence intervals are based on the difference in the LS Means from the final ANCOVA model.

Table 16 indicates that patients in the ITT experienced a 30.3% decrease in the mean morphine used in the postoperative period.

TABLE 16

Summary of Reduction in Morphine Use, ITT

| | Morphine Requirement | |
| --- | --- | --- |
| Post-Op-28 hours | Placebo (N = 84) | 800 mg (N = 95) |
| N | 84 | 95 |
| Mean (SD) | 60.1 (29.6) | 41.9 (26.9) |
| LS Means (SE) | 61.6 (5.9) | 45.2 (5.8) |
| Median | 58.5 | 38.0 |
| LS Means Difference (95% CI) | | −16.4 (−24.6, −8.1) |
| p-value vs Placebo[1] | | <0.001 |

[1]The analysis is based on a linear ANCOVA model with fixed effects for age group, weight group, randomization center, and treatment group. The p-values and 95% confidence intervals are based on the difference in the LS Means from the final ANCOVA model.

Table 17 indicates that patients in the EPP experienced a 33.3% decrease in the mean morphine used in the postoperative period.

TABLE 17

Summary of Reduction in Morphine Use, EEP

| | Morphine Requirement | |
| --- | --- | --- |
| Post-Op-28 hours | Placebo (N = 64) | 800 mg (N = 77) |
| N | 64 | 77 |
| Mean (SD) | 65.5 (28.2) | 43.7 (26.9) |
| LS Means (SE) | 61.8 (6.3) | 43.7 (5.9) |
| Median | 61.9 | 40.5 |
| LS Means Difference (95% CI) | | −18.1 (−27.2, −9.0) |
| p-value vs Placebo[1] | | <0.001 |

[1]The analysis is based on a linear ANCOVA model with fixed effects for age group, weight group, randomization center, and treatment group. The p-values and 95% confidence intervals are based on the difference in the LS Means from the final ANCOVA model.

Efficacy of the intravenous ibuprofen to treat post-operative pain was demonstrated by measuring the patient's self assessment of pain at rest using a visual analog scale during the post-operative period (study hour-6 through hour-28). VAS assessments were performed immediately following surgery and at hours 6, 8, 12, 16, 20, 24 and 28 (for the primary endpoint).

Patients receiving 800 mg intravenous ibuprofen experienced less pain, demonstrated by patients' self assessment of pain using a visual analog scale assessed at rest. Table 18 indicates that patients in the all treat population experienced a 31.8% decrease in the mean AUC-VAS in the post-operative period.

TABLE 18

Summary of Pain at Rest Measured with VAS, AT

| 6-28 hours | AUC (AT) | |
|---|---|---|
| (post-operative period) | Placebo (N = 86) | 800 mg (N = 99) |
| Mean (SD) | 910.9 (424.3) | 620.8 (401.0) |
| LS Means (SE) | 997.0 (83.6) | 728.0 (83.0) |
| Median | 905.1 | 566.0 |
| LS Means Difference (95% CI) | | −269.0 (−386.8, −151.2) |
| p-value vs Placebo[1] | | <0.001 |

[1]The analysis is based on a linear ANCOVA model with fixed effects for age group, weight group, randomization center, and treatment group. The p-values and 95% confidence intervals are based on the difference in the LS Means from the final ANCOVA model.

Table 19 indicates that patients in the ITT experienced a 31.9% decrease in the mean AUC-VAS in the post-operative period.

TABLE 19

Summary of Pain at Rest Measured with VAS, ITT

| 6-28 hours | AUC (ITT) | |
|---|---|---|
| (post-operative period) | Placebo (N = 84) | 800 mg (N = 95) |
| Mean (SD) | 911.1 (429.4) | 620.9 (418.6) |
| LS Means (SE) | 986.9 (87.1) | 722.2 (85.3) |
| Median | 905.1 | 561.9 |
| LS Means Difference (95% CI) | | −264.7 (−386.6, −142.9) |
| p-value vs Placebo[1] | | <0.001 |

[1]The analysis is based on a linear ANCOVA model with fixed effects for age group, weight group, randomization center, and treatment group. The p-values and 95% confidence intervals are based on the difference in the LS Means from the final ANCOVA model.

Table 20 indicates that patients in the EEP experienced a 26.9% decrease in the mean AUC-VAS in the post-operative period.

TABLE 20

Summary of Pain at Rest Measured with VAS, EEP

| 6-28 hours | AUC (EEP) | |
|---|---|---|
| (post-operative period) | Placebo (N = 64) | 800 mg (N = 77) |
| Mean (SD) | 867.3 (433.6) | 634.3 (429.4) |
| LS Means (SE) | 913.1 (97.2) | 714.9 (91.7) |
| Median | 884.4 | 550.7 |
| LS Means Difference (95% CI) | | −198.2 (−339.5, −56.9) |
| p-value vs Placebo[1] | | <0.001 |

[1]The analysis is based on a linear ANCOVA model with fixed effects for age group, weight group, randomization center, and treatment group. The p-values and 95% confidence intervals are based on the difference in the LS Means from the final ANCOVA model.

Efficacy of intravenous ibuprofen to treat post-operative pain was demonstrated by measuring the patient's self assessment of pain at rest using a verbal response during the post-operative period (study hour-6 through hour-28). VRS assessments were performed immediately following surgery and at hours 6, 8, 12, 16, 20, 24 and 28 (for the primary endpoint).

Patients receiving 800 mg intravenous ibuprofen experienced less pain, demonstrated by patients self assessment of pain using the AUC-VRS. Table 21 indicates that patients in the AT population experienced a 20.2% decrease in the mean AUC-VRS in the post-operative period.

TABLE 21

Summary of Pain at Rest Measured with VRS, AT

| 6-28 hours | AUC (AT) | |
|---|---|---|
| (post-operative period) | Placebo (N = 80) | 800 mg (N = 99) |
| Mean (SD) | 49.5 (18.2) | 39.5 (17.1) |
| LS Means (SE) | 51.8 (3.7) | 43.2 (3.6) |
| Median | 50.7 | 38.0 |
| LS Means Difference (95% CI) | | −8.6 (−13.6, −3.6) |
| p-value vs Placebo[1] | | <0.001 |

[1]The analysis is based on a linear ANCOVA model with fixed effects for age group, weight group, randomization center, and treatment group. The p-values and 95% confidence intervals are based on the difference in the LS Means from the final ANCOVA model.

Table 22 indicates that patients in the ITT experienced a 20.2% decrease in the mean AUC-VAS in the post-operative period.

TABLE 22

Summary of Pain at Rest Measured with VRS, ITT

| 6-28 hours | AUC (ITT) | |
|---|---|---|
| (post-operative period) | Placebo (N = 84) | 800 mg (N = 95) |
| Mean (SD) | 49.5 (18.2) | 39.5 (17.1) |
| LS Means (SE) | 51.8 (3.7) | 43.2 (3.6) |
| Median | 50.7 | 38.0 |
| LS Means Difference (95% CI) | | −8.6 (−13.6, −3.6) |
| p-value vs Placebo[1] | | <0.001 |

[1]The analysis is based on a linear ANCOVA model with fixed effects for age group, weight group, randomization center, and treatment group. The p-values and 95% confidence intervals are based on the difference in the LS Means from the final ANCOVA model.

Table 23 indicates that patients in the EEP experienced a 21.2% decrease in the mean AUC-VAS in the post-operative period.

TABLE 23

Summary of Pain at Rest Measured with VRS, EEP

| 6-28 hours | AUC (EEP) | |
|---|---|---|
| (post-operative period) | Placebo (N = 64) | 800 mg (N = 77) |
| Mean (SD) | 51.4 (17.1) | 40.5 (16.4) |
| LS Means (SE) | 52.8 (3.7) | 43.4 (3.5) |
| Median | 52.6 | 38.5 |
| LS Means Difference (95% CI) | | −9.4 (−14.8, −4.0) |
| p-value vs Placebo[1] | | <0.001 |

[1]The analysis is based on a linear ANCOVA model with fixed effects for age group, weight group, randomization center, and treatment group. The p-values and 95% confidence intervals are based on the difference in the LS Means from the final ANCOVA model.

The first dose of CTM was administered prior to the start of the surgical procedure. Therefore, a secondary objective evaluated the efficacy of intravenous ibuprofen compared to placebo for the treatment of post-operative pain demonstrated by patient's self assessment of pain using a visual analog scale immediately post-surgery.

Patients receiving 800 mg intravenous ibuprofen experienced less pain, demonstrated by patients' self assessment of pain using a visual analog scale immediately post-surgery. Patients in the AT population experienced a 15.8% decrease in the mean VAS at rest and a 13.9% decrease in the mean VAS with movement immediately post-surgery. Patients in the intent-to-treat population experienced a 16.5% decrease in the mean VAS at rest and a 14.3% decrease in the mean VAS with movement immediately post-surgery.

Patients in the efficacy evaluable population experienced a 14.7% decrease in the mean VAS at rest and a 13.6% decrease in the mean VAS with movement immediately post-surgery.

Efficacy of intravenous ibuprofen to treat post-operative pain was demonstrated by measuring the patient's self assessment of pain at rest or with movement using a visual analog scale during the post-operative period (post-op through hour-120). VAS assessments were performed immediately following surgery and at hours 6, 8, 12, 16, 20, 24, 28, 32, 38, 44, 50, 56, 62, 68 >72-96 and >96-120. While the majority of patients only received five doses, a time weighted AUC-VAS was also calculated for the post-op through 48 hour period. All non-missing VAS assessments taken from post-op through 48 hours were used in the calculation. No imputation was performed for missing values.

Patients receiving 800 mg intravenous ibuprofen experienced less pain, demonstrated by patients' self assessment of pain using a visual analog scale in the post-op through 48 hour period. Patients in the AT population experienced a 32.7% decrease in the mean AUC-VAS at rest and a 26.4% decrease in the mean AUC-VAS with movement in the post-op through 48 hour period.

Patients in the intent-to-treat population experienced a 32.7% decrease in the mean AUC-VAS at rest and a 26.4% decrease in the mean AUC-VAS with movement in the post-op through 48 hour period.

Patients in the efficacy evaluable population experienced a 27.6% decrease in the mean AUC-VAS at rest and a 23.7% decrease in the mean AUC-VAS with movement in the post-op through 48 hour period.

Additional measurements of efficacy were incidence of treatment failure, time to GI motility, time to resumption of ambulation, time to resumption of liquid intake, time to resumption of solid diet, and length of hospital stay. There were no significant differences between treatment groups for any of these additional measurements of efficacy; however, there was a numerical difference in the incidence of treatment failures between treatment groups.

Conclusions

In conclusion, 800 mg intravenous ibuprofen administered every 6 hours starting with the onset of anesthesia in orthopedic surgery patients reduces both pain and the need for morphine.

Compared to placebo, patients receiving 800 mg intravenous ibuprofen experienced a significant reduction in pain as measured by the VAS-AUC with movement for the post-operative period, study hours 6-28. In the all-treated population, there was a 25.8% reduction in mean VAS-AUC (hours 6-28, with movement) in patients receiving intravenous ibuprofen (p<0.001). In addition to experiencing less pain, patients receiving 800 mg intravenous ibuprofen used less morphine. In the all-treated population, there was a 30.9% reduction in mean morphine consumption in patients receiving intravenous ibuprofen for the post-operative period, study hours 6-28 (p<0.001).

There was also a significant reduction in pain as measured by the VAS at rest area under the curve and by the VRS for the post-operative period, study hours 6-28 (p<0.001). In the all-treated population, there was a 31.8% reduction in mean VAS-AUC (at rest) and a 20.2% reduction in mean VRS in patients receiving intravenous ibuprofen (p<0.001).

In addition to experiencing less pain, patients receiving 800 mg intravenous ibuprofen used less morphine. In the all-treated population, there was a 30.9% reduction in mean morphine consumption in patients receiving intravenous ibuprofen (p<0.001).

In the treatment-emergent adverse events experienced by at least three patients, there were significantly more patients in the intravenous ibuprofen group that experienced vomiting and significantly more patients in the placebo group that experienced dyspepsia. There was no statistically significant difference in the incidence of serious adverse events between the patients receiving placebo and the patients receiving 800 mg intravenous ibuprofen. There were no deaths reported for this study.

The results from this study demonstrate that intravenous ibuprofen is a safe and effective analgesic option for management of pain associated with orthopedic surgical procedures. Pre-surgical dosing results in significant differences in patients' self-assessment of pain immediately following surgery and a lower requirement for morphine to control pain. Safety profiles in treated patients were similar to the placebo group and there were no serious safety concerns.

CONCLUSION

It will be readily apparent to one of ordinary skill in the relevant arts that other suitable modifications and adaptations to the methods and applications described herein are suitable and may be made without departing from the scope of the invention or any embodiment thereof. While the invention has been described in connection with certain embodiments, it is not intended to limit the invention to the particular forms set forth, but on the contrary, it is intended to cover such alternatives, modifications and equivalents as may be included within the spirit and scope of the invention as defined by the following claims.

The invention claimed is:

1. A method for reducing surgical pain in human patients, consisting of
   (i) treating post-surgical pain by administering a first dose of intravenous ibuprofen solution in an amount of about 800 mg prior to the start of surgery on the patients,
   (ii) intravenously administering a further dose of 800 mg dose of intravenous ibuprofen about every six hours post-operatively to the patients at least until 24 hours after surgery and about every 6 hours from about 24 hours after surgery up to about 5 days after surgery; and
   (iii) administering morphine, an opioid analgesic, post-operatively to the patients in an amount which is reduced by about 20% or more within the first 24 hours after surgery than that typically required to control pain in human patients having undergone the same surgical procedure without said administration of ibuprofen, such that the human patients receiving intravenous ibuprofen experience about a 30% reduction in mean morphine consumption.

2. The method of claim 1, wherein the patients experience a significant reduction in pain as measured by the VAS with movement and/or the VAS at rest area under the curve for time points within the first 24 hours after surgery.

3. The method of claim 1, provides a reduction in side effects associated with the administration of opioid analgesics.

4. The method of claim 1, wherein the patient undergoes a surgical procedure selected from orthopedic surgery, gynecologic surgery, major abdominal surgery, lower abdominal, and general investigative surgery.

5. The method of claim 1, wherein the ibuprofen being intravenously administered after surgery improves the time to ambulation and significantly reduces pain scores in the patients, as compared to such patients receiving opioid analgesics without said administration of ibuprofen.

* * * * *